(12) United States Patent
Mohseni

(10) Patent No.: US 11,565,124 B2
(45) Date of Patent: Jan. 31, 2023

(54) METHOD AND SYSTEM FOR READING AND STIMULATING NEURONS THROUGH TISSUE USING LIGHT

(71) Applicant: Northwestern University, Evanston, IL (US)

(72) Inventor: Hooman Mohseni, Wilmette, IL (US)

(73) Assignee: Northwestern University, Evanston, IL (US)

( * ) Notice: Subject to any disclaimer, the term of this patent is extended or adjusted under 35 U.S.C. 154(b) by 146 days.

(21) Appl. No.: 16/638,218

(22) PCT Filed: Aug. 15, 2018

(86) PCT No.: PCT/US2018/000140
§ 371 (c)(1),
(2) Date: Feb. 11, 2020

(87) PCT Pub. No.: WO2019/035876
PCT Pub. Date: Feb. 21, 2019

(65) Prior Publication Data
US 2020/0360721 A1  Nov. 19, 2020

Related U.S. Application Data

(63) Continuation of application No. 62/545,769, filed on Aug. 15, 2017.

(51) Int. Cl.
*A61N 5/06* (2006.01)

(52) U.S. Cl.
CPC .......... *A61N 5/0622* (2013.01); *A61N 5/0601* (2013.01); *A61N 2005/063* (2013.01); *A61N 2005/0628* (2013.01); *A61N 2005/0665* (2013.01)

(58) Field of Classification Search
CPC ................ A61N 5/0622; A61N 5/0601; A61N 2005/0628; A61N 2005/063; A61N 2005/0665
See application file for complete search history.

(56) References Cited

U.S. PATENT DOCUMENTS 7,064,881 B2  6/2006  Mohseni
7,266,269 B2  9/2007  Koste et al.
(Continued)

OTHER PUBLICATIONS

Yotam Gil, Nadav Rotter, and Shiomi Arnon; "Feasibility of retroreflective transdermal optical wireless communication"; Applied Optics / vol. 51, No. 18 / Jun. 20, 2012 (Year: 2012).*
(Continued)

*Primary Examiner* — Brian T Gedeon
*Assistant Examiner* — Joshua Andrew Schum-Houck
(74) *Attorney, Agent, or Firm* — Bell & Manning, LLC

(57) ABSTRACT

A neural sensing system includes an interrogator that includes an optical head. The optical head is configured to transmit a light signal. The neural sensing system also includes a microprobe configured to contact tissue. The microprobe includes a transducer configured to receive the light signal and modulate the light signal with neural signal information sensed from the tissue. The microprobe also includes a retroreflector configured to reflect the modulated light signal back to the optical head of the interrogator.

20 Claims, 18 Drawing Sheets

(56) References Cited

U.S. PATENT DOCUMENTS

| | | | |
|---|---|---|---|
| 7,519,406 B2* | 4/2009 | Blank | A61B 5/14532 |
| | | | 600/310 |
| 8,475,506 B1* | 7/2013 | Bendett | A61N 5/0622 |
| | | | 607/89 |
| 9,360,428 B2 | 6/2016 | Tao et al. | |
| 2004/0082864 A1 | 4/2004 | Barbato | |
| 2009/0054955 A1* | 2/2009 | Kopell | A61N 5/0601 |
| | | | 607/88 |
| 2010/0262212 A1* | 10/2010 | Shoham | A61N 5/0601 |
| | | | 607/88 |
| 2010/0332161 A1 | 12/2010 | Bulumulla | |
| 2011/0108707 A1 | 5/2011 | Cui et al. | |
| 2016/0073887 A1* | 3/2016 | Lee | A61B 5/0084 |
| | | | 600/377 |
| 2016/0259059 A1 | 9/2016 | Mohseni | |

OTHER PUBLICATIONS

Hongki Kang, Jee-Yeon Kim, Yang-Kyu Choi and Yoonkey Nam "Feasibility Study of Extended-Gate-Type Silicon Nanowire Field-Effect Transistors for Neural Recording" Sensors 2017, 17, 705; doi:10.3390/s17040705 (Year: 2017).*

Samuel G. Rodriques, Adam H. Marblestone, Jorg Scholvin, Joel Dapello, Deblina Sarkar, Max Mankin, Ruixuan Gao, Lowell Wood, Edward S. Boyden, "Multiplexed neural recording along a single optical fiber via optical reflectometry," J. Biomed. Opt. 21(5), 057003 (2016), doi: 10.1117/1.JBO.21.5.057003. (Year: 2016).*

International Preliminary Report on Patentability issued in International Patent Application No. PCT/US2018/000140 dated Feb. 27, 2020, pp. 1-11.

Yin, M., Borton, D. A., Aceros, J., Patterson, W. R. & Nurmikko, A. V. A 100-channel hermetically sealed implantable device for chronic wireless neurosensing applications. *IEEE transactions on biomedical circuits and systems* 7, 115-128 (2013).PMC3904295.

Yin, M. et al. Wireless neurosensor for full-spectrum electrophysiology recordings during free behavior. *Neuron* 84, 1170-1182 (2014). 25482026.

Mitra, S., Putzeys, J., Lopez, C. M., Pennartz, C. A. & Yazicioglu, R. F. 24 Channel dual-band wireless neural recorder with activity-dependent power consumption. *Analog Integrated Circuits and Signal Processing* 83, 317-329 (2015).

Chae, M. S., Yang, Z., Yuce, M. R., Hoang, L. & Liu, W. A 128-channel 6 mW wireless neural recording IC with spike feature extraction and UWB transmitter. *IEEE Transactions on Neural Systems and Rehabilitation Engineering* 17, 312-321 (2009). 19435684.

Gao, H. et al. HermesE: A 96-Channel Full Data Rate Direct Neural Interface in 0.13$\mu$ m CMOS. *IEEE Journal of Solid-State Circuits* 47, 1043-1055 (2012).

Ghane-Motlagh, B. & Sawan, M. Design and implementation challenges of microelectrode arrays: a review. *Materials Sciences and Applications* 4, 483 (2013).

Lacour, S. P., Courtine, G. & Guck, J. Materials and technologies for soft implantable neuroprostheses. *Nature Reviews Materials* 1, 16063 (2016).

Chen, R., Canales, A. & Anikeeva, P. Neural recording and modulation technologies. *Nature Reviews Materials* 2, 16093 (2017).

Seo, D. et al. Wireless recording in the peripheral nervous system with ultrasonic neural dust. *Neuron* 91, 529-539 (2016).

Nacev, A. et al. Towards control of magnetic fluids in patients: directing therapeutic nanoparticles to disease locations. *IEEE Control Systems* 32, 32-74 (2012).

Wieser, W. et al. High definition live 3D-OCI in vivo: design and evaluation or a 4D OCI engine witn 1 GVoxel/s. *Biomedical optics express* 5, 2963-2977 (2014).

Ersen, A., Elkabes, S., Freedman, D. S. & Sahin, M. Chronic tissue response to untethered microelectrode implants in the rat brain and spinal cord. *Journal of neural engineering* 12, 016019 (2015).

Donaldson, K., Murphy, F. A., Duffin, R. & Poland, C. A. Asbestos, carbon nanotubes and the pleural mesothelium: a review of the hypothesis regarding the role of long fibre retention in the parietal pleura, inflammation and mesothelioma. *Particle and fibre toxicology* 7, 5 (2010).

Poland, C. A. et al. Carbon nanotubes introduced into the abdominal cavity of mice show asbestos-like pathogenicity in a pilot study. *Nature nanotechnology* 3, 423-428 (2008).

Schinwald, A. et al. The threshold length for fibre-induced acute pleural inflammation: shedding light on the early events in asbestos-induced mesothelioma. *Toxicological Sciences*, kfs171 (2012).

Ng, K. A., Greenwald, E., Xu, Y. P. & Thakor, N. V. Implantable neurotechnologies: a review of integrated circuit neural amplifiers. *Medical & biological engineering & computing* 54, 45-62 (2016).

Stelzer, E. H. Light microscopy: Beyond the diffraction limit? *Nature* 417, 806-807 (2002).

Mohseni, H., An, H., Shellenbarger, Z., Kwakernaak, M. & Abeles, J. Highly linear and efficient phase modulators based on GaInAsP—InP three-step quantum wells. *Applied Physics Letters* 86, 031103 (2005).

Mohseni, H., Chan, W., An, H., Ulmer, A. & Capewell, D. in *Defense and Security*. 191-198 (International Society for Optics and Photonics).

Bonakdar, A. & Mohseni, H. Hybrid optical antenna with high directivity gain. *Optics letters* 38, 2726-2728 (2013).

Wu, W., Katsnelson, A., Memis, O. G. & Mohseni, H. A deep sub-wavelength process for the formation of highly uniform arrays of nanoholes and nanopillars. *Nanotechnology* 18, 485302 (2007).

Szuts, T. A. et al. A wireless multi-channel neural amplifier for freely moving animals. *Nature neuroscience* 14, 263-269 (2011).

Seo, D., Carmena, J. M., Rabaey, J. M., Alon, E. & Maharbiz, M. M. Neural dust: An ultrasonic, low power solution for chronic brain-machine interfaces. *arXiv preprint arXiv*:1307.2196 (2013).

Kherlopian, A. R. et al. A review of imaging techniques for systems biology. *BMC systems biology* 2, 1 (2008).

Groothuis, J., Ramsey, N. F., Ramakers, G. M. & van der Plasse, G. Physiological challenges for intracortical electrodes. *Brain stimulation* 7, 1-6 (2014).

Szarowski, D. et al. Brain responses to micro-machined silicon devices. *Brain research* 3, 23-35 (2003).

Fink, M. et al. Time-reversed acoustics. *Reports on progress in Physics* 63, 1933 (2000).

Mosk, A. P., Lagendijk, A., Lerosey, G. & Fink, M. Controlling waves in space and time for imaging and focusing in complex media. *Nature photonics* 6, 283-292 (2012).

Drexler, W. & Fujimoto, J. G. *Optical coherence tomography: technology and applications*. (Springer Science & Business Media, 2008).

Podoleanu, A. G. Optical coherence tomography. *The British journal of radiology* (2014).

Fercher, A. F., Drexler, W., Hitzenberger, C. K. & Lasser, T. Optical coherence tomography-principles and applications. *Reports on progress in physics* 66, 239 (2003).

Charschan, S. S. & Rockwell, B. A. Update on ANSI Z136. 1. *Journal of Laser Applications* 11, 243-247 (1999).

Gower, M. KrF laser amplifier with phase-conjugate Brillouin retroreflectors. *Optics letters* 7, 423-425 (1982).

Snyder, J. Paraxial ray analysis of a cat's-eye retroreflector. *Applied optics* 14, 1825-1828 (1975).

Takatsuji, T., Goto, M., Osawa, S., Yin, R. & Kurosawa, T. Whole-viewing-angle cat's-eye retroreflector as a target of laser trackers. *Measurement Science and Technology* 10, N87 (1999).

Wilcox, D. L. & Berg, M. Microsphere fabrication and applications: an overview. *MRS Online Proceedings Library Archive* 372 (1994).

Figueiredo, J. et al. Optical modulation at around 1550 nm in an InGaAlAs optical waveguide containing an InGaAs/AlAs resonant tunneling diode. *Applied physics letters* 75, 3443-3445 (1999).

Wang, Q. et al. 1550 nm transmissive/reflective surface-normal electroabsorption modulator arrays. *Electronics Letters* 42, 47-49 (2006).

(56) References Cited

OTHER PUBLICATIONS

Satzke, K. et al. Ultrahigh-bandwidth (42 GHz) polarisation-independent ridge waveguide electroabsorption modulator based on tensile strained InGaAsP MQW. *Electronics Letters* 31, 2030-2032 (1995).
Mohseni, H., Chan, W., An, H., Ulmer, A. & Capewell, D. in *Integrated Optoelectronic Devices* 2006. 61270D-61270D-61211 (International Society for Optics and Photonics).
Hassan Nia, I., Fathipour, V. & Mohseni, H. Observation or suppressed Auger Mechanism in type-I quantum well structures with delocalized electron-hole wavefunctions. *AIP Advances* 5, 087138 (2015).
Nia, I. H. & Mohseni, H. A proposal for Coulomb assisted laser cooling of piezoelectric semiconductors. *Applied Physics Letters* 105, 042102 (2014).
Wheaton, S. et al. Open architecture time of fight 3D SWIR camera operating at 150 MHz modulation frequency. *Optics Express* 25, 19291-19297 (2017).
Kim, T.-i et al. Injectable, cellular-scale optoelectronics with applications for wireless optogenetics. *Science* 340, 211-216 (2013).
Wakita, K. et al. High-speed InGaAlAs/InAlAs multiple quantum well optical modulators. *Journal of Lightwave Technology* 3, 1027-1032 (1990).
Ido, T. et al. Ultra-high-speed multiple-quantum-well electroabsorption optical modulators with integrated waveguides. *Journal of lightwave technology* 14, 2026-2034 (1996).
Dagli, N. Wide-bandwidth lasers and modulators for RF photonics. *IEEE Transactions on microwave theory and techniques* 47, 1151-1171 (1999).
Nia, I. H. & Mohseni, H. in *SPIE OPTO.* 93800E-93800E-93809 (International Society for Optics and Photonics).
Fahim, F., Fathipouri, V., Deptuch, G. & Mohseni, H. in Circuits and Systems (ISCAS), 2015 *IEEE International Symposium on.* 682-685 (IEEE).
Fahim, F., Deptucha, G. W., Hoffa, J. R. & Mohseni, H. in *Proc. of SPIE* vol. 955517-955511.
Fahim, F., Deptucha, G. W., Hoffa, J. R. & Mohseni, H. in *Proc. of SPIE* vol. 95550M-95551.
Memis, O. G., Kohoutek, J., Wu, W., Gelfand, R. M. & Mohseni, H. A Short-Wave Infrared Nanoinjection Imager With 2500 A/W Responsivity and Low Excess Noise. *IEEE Photonics Journal* 2, 858-864 (2010).
Memis, O. G., Kohoutek, J., Wu, W., Gelfand, R. M. & Mohseni, H. in *Sensors*, 2010 IEEE. 128-131 (IEEE).
Memis, O. G., Kohoutek, J., Wu, W., Gelfand, R. M. & Mohseni, H. Signal-to-noise performance of a short-wave infrared nanoinjection imager. *Optics letters* 35, 2699-2701 (2010).
Rezaei, M., Nia, I. H., Bonakdar, A. & Mohseni, H. Simple telecentric submillimeter lens with near-diffraction-limited performance across an 80 degree field of view. *Applied optics* 55, 8752-8756 (2016).
Dombeck, D. A., Harvey, C. D., Tian, L., Looger, L. L. & Tank, D. W. Functional Imaging of hippocampal place cells at cellular resolution during virtual navigation. *Nature neuroscience* 13, 1433-1440 (2010).PMC2967725.
Dombeck, D. A., Khabbaz, A. N., Collman, F., Adelman, T. L. & Tank, D. W. Imaging large-scale neural activity with cellular resolution in awake, mobile mice. *Neuron* 56, 43-57 (2007). PMC2268027.
Dombeck, D. A., Graziano, M. S. & Tank, D. W. Functional clustering of neurons in motor cortex determined by cellular resolution imaging in awake behaving mice. *Journal of Neuroscience* 29, 13751-13760 (2009).PMC2872549.
Sheffield, M. E. & Dombeck, D. A. Calcium transient prevalence across the dendritic arbor predicts place field properties. *Nature* 517, 200 (2015).PMC4289090.
Howe, M. & Dombeck, D. Rapid signaling in distinct dopaminergic axons during locomotion and reward. *Nature* 535, 505 (2016). PMC4970879.

Heys, J. G., Rangarajan, K. V. & Dombeck, D. A. The functional micro-organization of grid cells revealed by cellular-resolution imaging. *Neuron* 84, 1079-1090 (2014).
Biran, R., Martin, D. C. & Tresco, P. A. Neuronal cell loss accompanies the brain tissue response to chronically implanted silicon microelectrode arrays. *Experimental neurology* 195, 115-126 (2005).
Silver, J. & Miller, J. H. Regeneration beyond the glial scar. *Nature reviews. Neuroscience* 5, 146 (2004).
Polikov, V. S., Tresco, P. A. & Reichert, W. M. Response of brain tissue to chronically implanted neural electrodes. *Journal of neuroscience methods* 148, 1-18 (2005).
Woerly, S. Restorative surgery of the central nervous system by means of tissue engineering using NeuroGel implants. *Neurosurgical review* 23, 59-77 (2000).
Heilman, K. M. & Valenstein, E. Frontal lobe neglect in man. *Neurology* 22, 660-660 (1972).
Cabrera DeBuc, D. & Li, Y. A Review on Recent Patents on Optical Coherence Tomography Applications in Ophthalmology. *Recent Patents on Medical Imaging* 2, 2-5 (2012).
Drexler, W. & Fujimoto, J. G. *Optical coherence tomography: technology and applications.* (Springer, 2015).
Ramaswamy, B. et al. Movement of magnetic nanoparticles in brain tissue: mechanisms and impact on normal neuronal function. *Nanomedicine: Nanotechnology, Biology and Medicine* 11, 1821-1829 (2015).
Crowther, L. J. et al. Transcranial magnetic stimulation: Improved coil design for deep brain investigation. *Journal of Applied Physics* 109, 07B314 (2011).
Rosensweig, R. E. *Ferrohydrodynamics.* (Courier Corporation, 2013).
Fleisch, D. *A student's guide to Maxwell's equations.* (Cambridge University Press, 2008).
Basak, S. et al. Transport characteristics of nanoparticle-based ferrofluids in a gel model of the brain. *International journal of nanomedicine* 4, 9 (2009).
Holligan, D., Gillies, G. & Dailey, J. Magnetic guidance of ferrofluidic nanoparticles in an in vitro model of intraocular retinal repair. *Nanotechnology* 14, 661 (2003).
Kuhn, S. J., Hallahan, D. E. & Giorgio, T. D. Characterization of superparamagnetic nanoparticle interactions with extracellular matrix in an in vitro system. *Annals of biomedical engineering* 34, 51-58 (2006).
Erni, S., Schürle, S., Fakhraee, A., Kratochvil, B. E. & Nelson, B. J. Comparison, optimization, and limitations of magnetic manipulation systems. *Journal of Micro-Bio Robotics* 8, 107-120 (2013).
Martin, E. T. et al. Magnetic resonance imaging and cardiac pacemaker safety at 1.5-Tesla. *Journal of the American College of Cardiology* 43, 1315-1324 (2004).
Krieger, S. N., Streicher, M. N., Trampel, R. & Turner, R. Cerebral blood volume changes during brain activation. *Journal of Cerebral Blood Flow & Metabolism* 32, 1618-1631 (2012).
Jozwiak, A., Liu, Y., Yang, Y. & Gates, M. A. Development of a stereotaxic device for low impact implantation of neural constructs or pieces of neural tissues into the mammalian brain. *BioMed research international* 2014 (2014).
Katchinskiy, N., Goez, H. R., Dutta, I., Godbout, R. & Elezzabi, A. Y. Novel method for neuronal nanosurgical connection. *Scientific reports* 6 (2016).
Lim, H. G. et al. Calibration of Trapping Force on Cell-Size Objects from Ultrahigh-Frequency Single-Beam Acoustic Tweezer. *IEEE transactions on ultrasonics, ferroelectrics, and frequency control* 63, 1988-1995 (2016).
Lerosey, G. & Fink, M. Acousto-optic imaging: Merging the best of two worlds. *Nature Photonics* 7, 265-267 (2013).
Xu, X., Liu, H. & Wang, L. V. Time-reversed ultrasonically encoded optical focusing into scattering media. *Nature photonics* 5, 154-157 (2011).PMC3083021.
Resink, S. G., Boccara, A. C. & Steenbergen, W. State-of-the art of acousto-optic sensing and imaging of turbid media. *Journal of biomedical optics* 17, 0409011-04090110 (2012).22559674.
Resink, S., Hondebrink, E. & Steenbergen, W. Towards acousto-optic tissue imaging with nanosecond laser pulses. *Optics express* 22, 3564-3571 (2014).24663646.

(56) References Cited

OTHER PUBLICATIONS

Fang, H. et al. Capacitively coupled arrays or multiplexed flexible silicon transistors for long-term cardiac electrophysiology. *Nature Biomedical Engineering* 1, 0038 (2017).
Shin, G. et al. Flexible Near-Field Wireless Optoelectronics as Subdermal Implants for Broad Applications in Optogenetics. *Neuron* 93, 509-521 (2017).
Lu, L. et al. Wireless optoelectronic photometers for monitoring neuronal dynamics in the deep brain. *Proceedings of the National Academy of Sciences* 115 E1374-E1383, (2018).
The International Search Report and the Written Opinion dated Nov. 19, 2019 for International patent application No. PCT/US2019/050150; pp. 1-7.
Hassani et al., "Evaluation of the Returned Electromagnetic Signal from Retrorefectors in Turbid Media," *Nature* (Apr. 25, 2019) 9: 6550. [retrieved on Oct. 23, 2019], Retrieved from the Internet. URL: http://www.bisol.northwestern.edu/web/papers/skyler_iman_sci_report.pedf.
Horstmeyer et al., "Guidestar-assisted wavefront-shaping methods for focusing light into biological tissue," *Nat Photonics* 2015; 9: 563-571. [retrieved on Oct. 25, 2019], Retrieved from the Internet. URL: doi:10.1038/nphoton.2015.140. Entire document.

\* cited by examiner

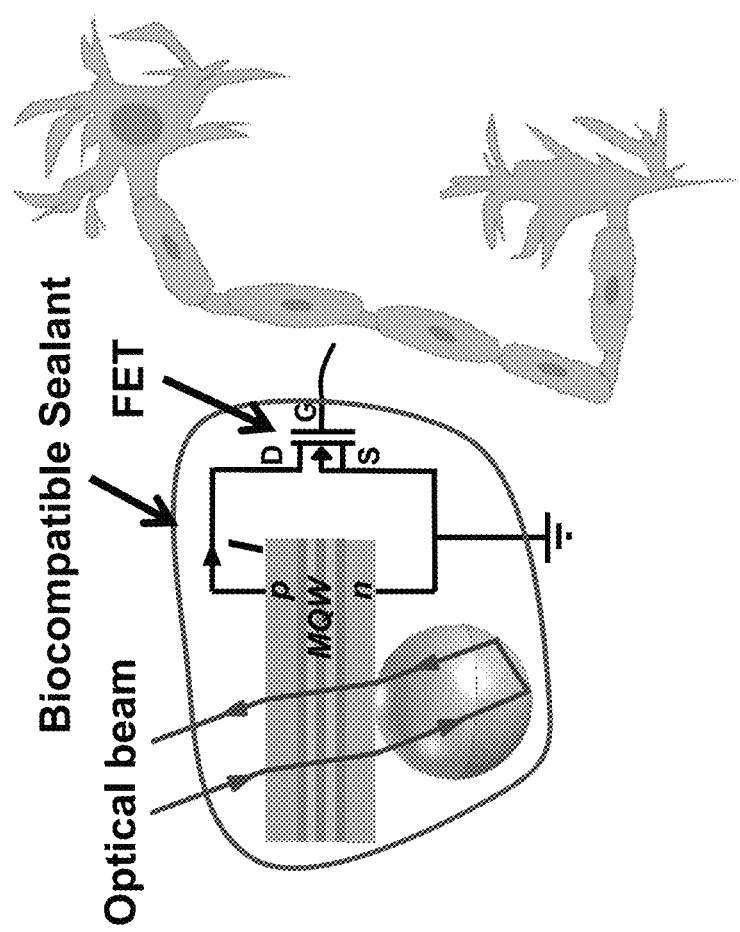
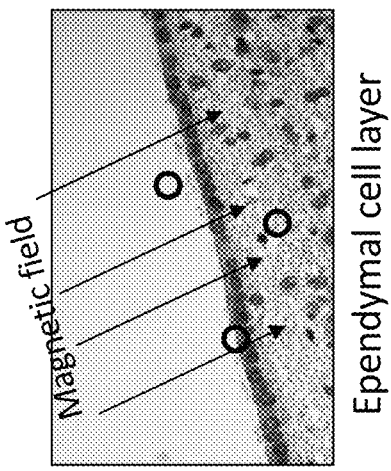
FIG. 2D
FIG. 2E

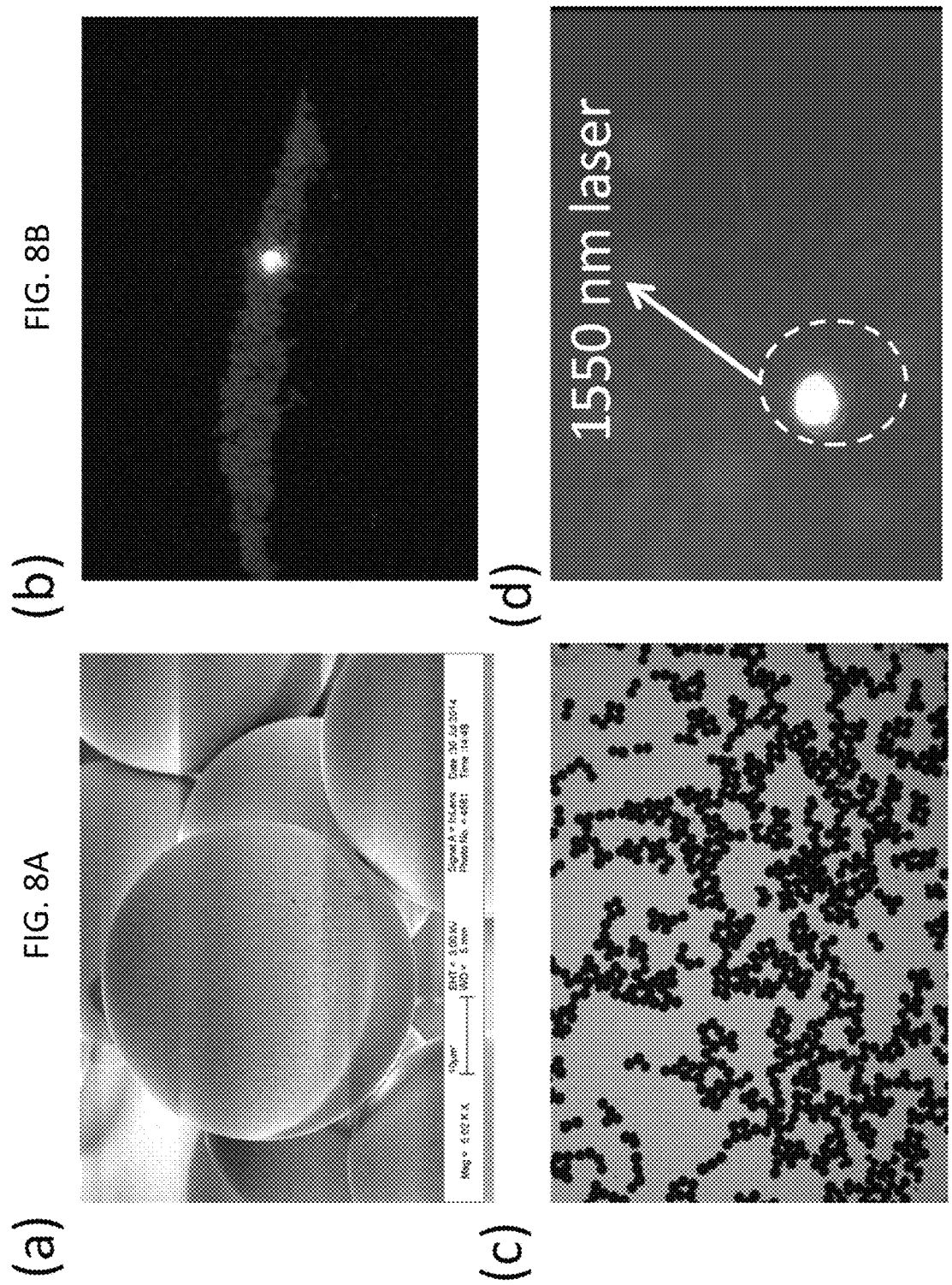

METHOD AND SYSTEM FOR READING AND STIMULATING NEURONS THROUGH TISSUE USING LIGHT

CROSS-REFERENCE TO RELATED APPLICATION

This application claims the priority benefit as a national stage entry of PCT App. No. PCT/US2018/000140 filed on Aug. 15, 2018, which claims the priority benefit of U.S. Provisional Patent App. No. 62/545,769 filed on Aug. 15, 2017, the entire disclosures of which are incorporated herein by reference.

REFERENCE TO GOVERNMENT RIGHTS

This invention was made with government support under ECCS-1310620 awarded by the National Science Foundation. The government has certain rights in the invention.

BACKGROUND

Neural sensing refers to the sensing of electrical signals generated by neurons within the brain, and can be used to monitor brain activity and neural responses to various stimuli. Neural sensing can also be used to diagnose various health conditions such as sleep disorders, brain trauma, epilepsy, etc. Traditional neural sensing is performed using a wired array of electrodes placed on the scalp. For example, in electroencephalography (EEG), a non-invasive array of electrodes is positioned on the scalp of a patient and used to detect electrical signals. Other types of neural sensing, such as electrocorticography, are invasive and involve using electrodes that are placed directly on the exposed surface of the brain.

SUMMARY

An illustrative neural sensing system includes an interrogator that includes an optical head. The optical head is configured to transmit a light signal. The neural sensing system also includes a microprobe configured to contact tissue. The microprobe includes a transducer configured to receive the light signal and modulate the light signal with neural signal information sensed from the tissue. The microprobe also includes a retroreflector configured to reflect the modulated light signal back to the optical head of the interrogator.

An illustrative method of sensing data includes transmitting, by an optical head of an interrogator, a light signal. The method also includes receiving, by a transducer of a microprobe that is in contact with tissue, the light signal from the optical head. The method also includes modulating, by the transducer, the light signal with neural signal information sensed from the tissue. The method further includes reflecting, by a retroreflector of the microprobe, the modulated light signal back to the optical head of the interrogator.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 2D depicts a general design of a microprobe in accordance with another illustrative embodiment.

FIG. 2E depicts use of a magnetic field to move microprobes in accordance with an illustrative embodiment.

FIG. 8A is a high magnification image of a retroreflector half-coated with metal in accordance with an illustrative embodiment.

FIG. 8B depicts the reflection of a visible laser (with a wavelength of 850 nm) from an island of microsphere retroreflectors in accordance with an illustrative embodiment.

FIG. 8C is an optical image of a large number of sphere retroreflectors produced in accordance with an illustrative embodiment.

FIG. 8D depicts the retroreflection of a 1550 nm laser from a sphere retroreflector buried under a 300 μm brain slice in accordance with an illustrative embodiment.

DETAILED DESCRIPTION

The most commonly used methods for wired neural sensing include wired microelectrode arrays. Wireless neural sensing methods based on optogenetics are also used in some implementations. Traditional wired microelectrode arrays have significant limitations due to the negative impacts of the microneedles on brain tissue over time. The number of needles is also limited and cannot be easily scaled above thousands. While optogenetic-based approaches have been successful due to their tether-free nature, scaling the read point to above several hundred proves to be challenging due to the high optical (laser) power needed, and the adverse effect (i.e., heat) from such power levels.

The present disclosure relates to a new method which has been developed to read and stimulate neural signals wirelessly using infrared light. This method is highly scalable, and efficient. The energy utilized to transmit a bit of information is very small, and hence the heat dissipation inside the brain tissue remains small even at a high transmission rate. Experiments have demonstrated that tens of thousands of neurons can be read simultaneously, and with little timing delay using the approaches described herein. The large number of neurons, combined with the small timing delay, enable sophisticated neural engineering.

More specifically, described herein are systems and methods for bi-directional low-latency data transmission of light through tissue to record activities of, and/or provide stimulation to, a large number of neurons. The proposed methods and systems can be used in both central nervous system and peripheral nervous system, and for a variety of applications. The proposed system includes two primary components, an interrogator and a plurality of microprobes. The interrogator is an intermediate interface between the outside world (e.g. a computer) and the microprobes. The interrogator can communicate with a large number of microprobes, exceeding hundreds of thousands, with very small timing latency and a high fidelity. The microprobes interface neurons via different modalities including electrical, magnetic, chemical, etc. There are many applications for the proposed system including pain management, direct brain-machine link for quadriplegics, prosthetics, diagnosis, etc. The proposed system will also enable massive brain-machine-brain interface for the first time with a broad range of applications. Specific examples of the electrical interface are described herein.

Figure 1B:
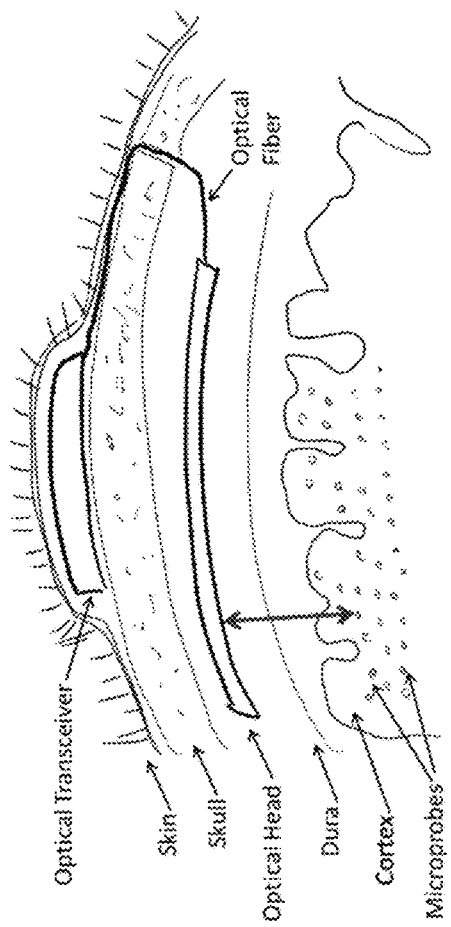
FIG. 1B is a cross-section view of the neural detection system implanted in a patient in accordance with an illustrative embodiment.
Figure 1A:
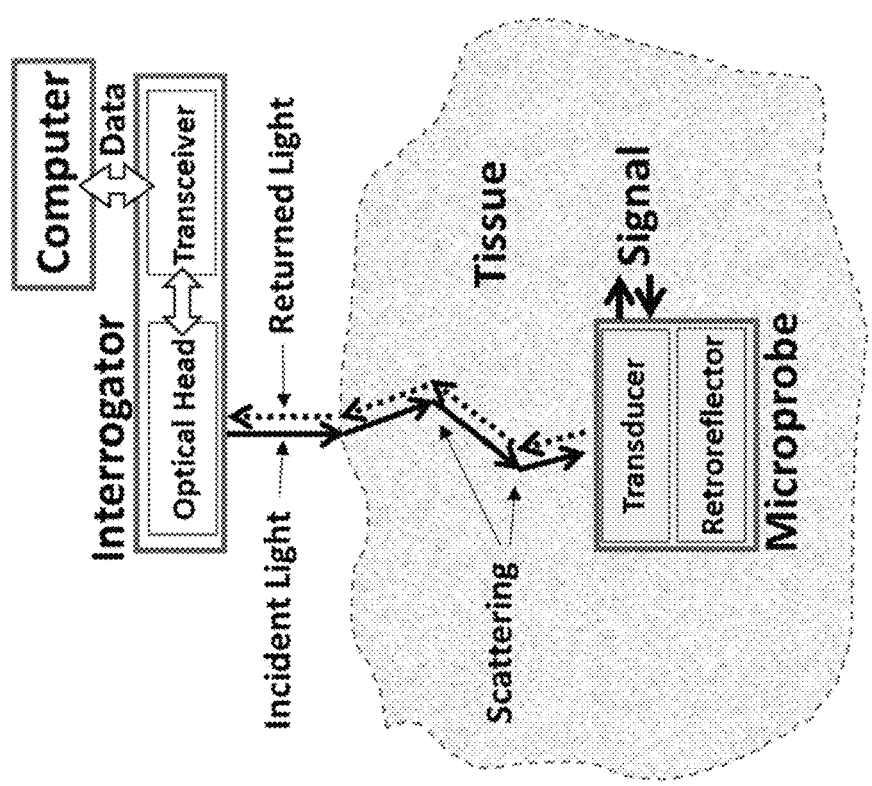
FIG. 1A depicts communication via an optical link between an interrogator and microprobes of a neural detection system in accordance with an illustrative embodiment.

FIG. 1A depicts communication via an optical link between an interrogator and microprobes of a neural detection system in accordance with an illustrative embodiment. FIG. 1B is a cross-section view of the neural detection system implanted in a patient in accordance with an illustrative embodiment. As shown in FIG. 1A, the interrogator includes an optical head and a transceiver, and each microprobe includes a transducer and a retroreflector. In alternative embodiments, the interrogator and/or microprobe can include additional or different components. Incident light is generated by the optical head and directed to the microprobe. The interrogator can send data to microprobes by coding the incident light. Specifically, the microprobe can transmit data to the interrogator by modulating the incident beam of light. The retroreflector then back-reflects the modulated beam and produces a strong returned signal at the interrogator.

As discussed in more detail below, the interrogator uses scanning and coherent interference methods to communicate with a specific three-dimensional zone of space at a given time. As a result, the interrogator can collect and transmit data from/to a 4-dimensional spatio-temporal space of interest. This property allows one interrogator to communicate with a large number of microprobes, while tracking their specific locations. The communication with microprobes can be sequential, parallel, or a combination of both sequential and parallel. The proposed systems and methods allow for high-fidelity communication between hundreds of thousands of microprobes and a single interrogator—an ability that is better than the existing technologies by several orders of magnitude. The latency of the whole system is less than the sampling time of each microprobe, which is typically less than a millisecond. In some embodiments, multiple interrogators can be incorporated into the system and used to communicate with different zones of the brain.

The transceiver of the interrogator is configured to convert bi-directional data from the outside world (e.g. a computer) to an all-optical form that is then communicated via the optical head to the microprobes. The transceiver can use existing methods of communication to interface with the outside world, including optical fibers, electrical cables, radio links, or optical free-space links.

The optical head sends/receives light to/from the microprobes. In an illustrative embodiment, the light used can be coherent infrared light at ~200 THz. Alternatively, a different type of light and/or light frequency may be used. The optical head can be made of conventional bulk optical components, such as lenses and optical scanners, and placed far from the tissue. Also, the optical head can be made from thin and conformal passive and/or active optical components located close to, on, or inside the tissue. For example, optical head can be located under the skull as shown in FIG. 1B. In an illustrative embodiment, the optical head and the optical transceiver are connected via free-space or guided optical links (e.g. optical fibers). The main function of the optical head is efficient coupling of light to/from the microprobes. The use of an asymmetric infrared link allows ultra-low power (e.g., nano-Watt) on the tissue side, and the use of optical pseudo-time reversal produces efficient transmission through tissue.

The microprobes are located on, or implanted inside the tissue and sense the neural activities via electrical, chemical, magnetic, and other modalities, and transmit the identified signal to the interrogator. The interrogator can also transmit data to the same or a different set of microprobes. Some of these data could be used to control the state of the microprobes, others can modulate neural stimuli, such as electrical and chemical. In the implementation of FIG. 1B, the microprobes are positioned in the cortex, and the optical head of the interrogator is positioned between the dura and the skull. The optical transceiver of the interrogator is positioned between the skull and skin of the body, and is connected to the optical head via an optical fiber. In alternative embodiments, other positioning arrangements may be used. For example, in an alternative embodiment, the microprobes may be the only component of the system that are implanted within the body. The other system components such as the interrogator can be remote from the body or in contact with an outer surface of the body's skin. In one embodiment, a small portion of the skull may be removed to create a window through which the light signals can propagate to/from the brain tissue. In another alternative embodiment, the light signals can propagate to/from the brain tissue through the intact skin and skull of the body.

As depicted in FIG. 1A, the microprobes each include a retroreflector and a transducer. The retroreflector returns light beams incident to the microprobe from different angles back to the same directions. The microprobes can be built in a variety of forms, including microspheres that are half-coated with a reflecting layer, an hourglass lens with a reflective coating on one side, corner-cubes, etc. The transducer converts the neural signals (electrical, chemical, magnetic, etc.) using optical modulation (change of optical transmission, phase, polarization, etc.) The optical modulation can be of analog nature, or digital nature. Described herein are specific examples of a transducer that converts the electrical neural activities to the optical transmission in analog form. As detailed in the following, this example is based on a single transistor and an electro-absorptive modulator and involves no other component. In an illustrative embodiment, the optical beam sent by the interrogator powers the transistor via the photovoltaic effect of the electro-absorptive modulator, as described herein. It is therefore shown that this realization is completely self-powered.

In embodiments in which the microprobes are self-powered, the microprobes can include other components such as power harvesting components and electronics. The power harvesting can be optical (i.e. similar to a solar cell), or utilize other modalities such as RF, chemical, and acoustic. The electronics can be used for power regulation, digital signal processing, coding, etc. These components can include many of the existing technologies commonly used for digital communication.

The data transmission from microprobes to the interrogator is based on modulation and retro-reflection. In an illustrative embodiment, the interrogator sends light to microprobes, which is first modulated with the neural data using the transducer, and then returned back via the retroreflector inside the microprobes as shown in FIG. 1A. The data can be either in analog or digital form. The interrogator decodes the modulated light to recover the data (analog or digital) and sends it to the computer. Alternatively, the interrogator can be configured to store the decoded data in a local memory for later transfer to the computer or another storage device. The incident light can be used to harvest power for microprobe operation, as discussed with reference to the realization for an optoelectronic transducer. However, power harvesting is not always included. For example, power harvesting may not be used in the case of a magneto-optic transducer detecting the local magnetic field produced by the neural currents.

The data transmission from the interrogator to microprobes is based on modulating the incident light beam with the data. The wavelength of this light beam can be the same used for the data transmission from microprobe to interrogator, if common communication protocols are used. However, this approach shares the bandwidth. The wavelength can also be different, such that a photodetector in the microprobe that is only sensitive to a given wavelength converts the modulated light to the data in analog or digital form. The modulator used enables low energy per bit consumption, for example 0.7 fJ/bit.

Other implantable wireless technologies for communicating through tissue include radio frequency (RF) links and acoustic (ultrasound) links. However, the proposed system has several fundamental advantages compared with the RF links. The proposed system enables efficient spatial coding. Optical beams in the tissue optical window (e.g., near infrared (NIR) and short-wave infrared (SWIR)) can stay quite directional within a substantial depth, due to the large isotropic scattering coefficient $g=\sim 0.9$ of the tissues. This property allows 4D spatio-temporal communication with microprobes, as detailed herein. Also, methods to improve the beam focusing, such as adaptive optics, can be used to significantly improve the coupling of light into the microprobes.

As compared to other wireless techniques, the proposed system also provides low link loss. The micron size of the wavelength in an optical link allows for much more efficient transmitter and receiver antennas within a small footprint of microprobes implanted at millimeter depths. The optical link not only has a lower link loss, compared to RF, but also has a much better power harvesting efficiency at microprobe dimensions below 100 micrometers ($\mu$m). Additionally, the proposed system provides high immunity to external interference. Unlike RF, short wavelength infrared cannot penetrate the skull. While humans are immersed in intense RF sources with digital components (e.g. mobile phones, WiFi, Bluetooth, etc.), infrared sources are mostly natural and do not carry high frequency data components. Therefore, even if light could penetrate inside the skull, it can be easily filtered.

The proposed systems also have several advantages over using ultrasound to communicate with the so-called neural dusts. Compared to ultrasound, the proposed systems enable ultra-high bandwidth. The optical carrier proposed herein is able to carry a massive amount of data compared to an acoustic carrier, due to a much higher optical carrier frequency (tens or hundreds of THz) compared with RF carriers (several GHz to tens of GHz). This is an important property that allows aggregation of all data from/to millions of neurons into a single beam of light that could be carried via an optical fiber through the skull. Also, to enhance the coupling of ultrasound to piezo-electric parts (e.g. inside the neural dust), one has to use resonance coupling. This approach further reduces the acoustic bandwidth.

As compared to other techniques, the proposed system also provides the ability to shrink the microprobes down to dimensions that are smaller than neurons. Infrared light (e.g., NIR and SWIR) can be focused into a few microns in the tissue readily. It has been shown that this property allows microprobes to be smaller than neurons. Many studies suggest large implanted objects lead to stronger tissue reaction and scar cell formation. Ultrasound waves however, cannot be focused to such small dimensions due to their significantly longer wavelengths, and the resulted probes face fundamental physics limitations when scaled to a few tens of microns.

Figure 2A:
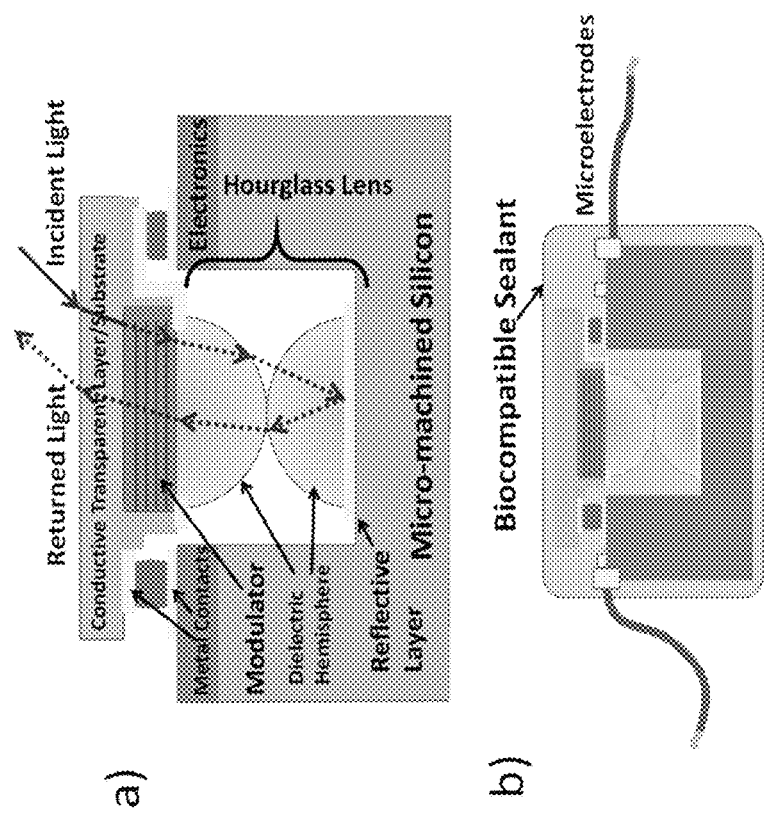
FIG. 2A depicts a general design of a microprobe based on electrical communication with neurons in accordance with an illustrative embodiment.
Figure 2B:
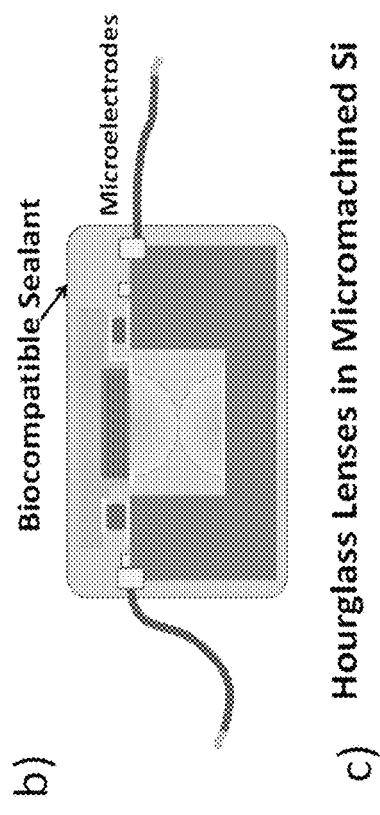
FIG. 2B depicts microelectrodes of a microprobe in accordance with an illustrative embodiment.
Figure 2C:
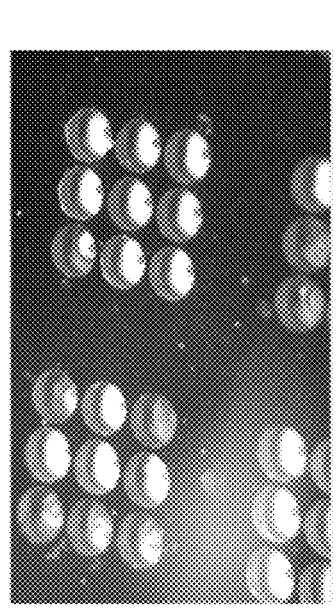
FIG. 2C depicts a micro-machined silicon wafer with an hourglass lens in accordance with an illustrative embodiment.

FIG. 2A depicts a general design of a microprobe based on electrical communication with neurons in accordance with an illustrative embodiment. The main components of the microprobe are a retroreflector, a transceiver made of an electroabsorptive modulator, and electronics. The microprobe components can be integrated using existing microprocessing and packaging technologies, including silicon micromachining, flip-chip bonding, indium bump-bonding, and standard lithography methods. The packaged microprobe can also be encapsulated (i.e., hermetically sealed) in biocompatible sealants that are transparent to the light wavelength used for communication between the interrogator and the microprobes, which is typically in the near infrared (NIR), or short-wave infrared (SWIR) bands. The electrical sensing conductors, called microelectrodes are extended outside the microprobe device to electrically connect the tissue to the inside of the device. FIG. 2B depicts microelectrodes of a microprobe in accordance with an illustrative embodiment. The microelectrodes extend from the hermetically sealed portion of the microprobe and are used to couple electrical signals between the tissue and the other components of the microprobe. As one example, a micromachined silicon wafer with an hourglass lens can be used to form the microprobes. FIG. 2C depicts a micromachined silicon wafer with an hourglass lens in accordance with an illustrative embodiment. The microprobe can transmit the data in analog form or digital form, depending on the electronics used. FIG. 2D depicts a general design of a microprobe in accordance with another illustrative embodiment.

In an illustrative embodiment, microprobes can be delivered into and removed from tissue using a lumbar puncture technique. Lumbar puncture is a routine and safe procedure, done approximately 500,000 times per year in the United Sates, that provides access to cerebrospinal fluid (CSF) in subarachnoid space and connected to brain ventricles. The brain ventricles are lined by an ependymal cell layer. In an illustrative embodiment, microprobes are injected into the CSF via a lumbar puncture procedure, and diffusion or magnetic driven steering is used to direct (i.e., move) the implanted microprobes to the ventricle of interest.

As discussed above, once implanted, magnetic guiding can be used to move the microprobes such that the microprobes penetrate the ependymal cell layer through oscillatory magnetic field forces. FIG. 2E depicts use of a magnetic field to move microprobes in accordance with an illustrative embodiment. Magnetic guiding of nano and micro particles has been demonstrated in different tissues, including brain tissue, and at depths of several centimeters. A simulation showed that micron size microprobes can be moved with even better control than nano-particles due to a larger volume to surface ratio. Small magnetic fields (e.g., B=250 mT) can produce a velocity of tens of $\mu$m/second, with high accuracy. Much higher velocities can be achieved for safe magnetic fields up to ~1.5 T.

Evaluations have also shown the ability to communicate with microprobes through an intact human skull for imaging applications. Additionally, advanced wavefront correction has demonstrated diffraction-limited micron resolution through an intact skull and dura of rodents. The retroreflector used exhibits a bright, natural 'guide star' effect that enhances imaging capabilities, and the technology works with beam sizes that are well above the diffraction limit. Additionally, reducing scattering and absorption of light through skin and skull using optical clearing has been demonstrated and can be used to enhance optical communication deep within the brain.

Figure 3B:
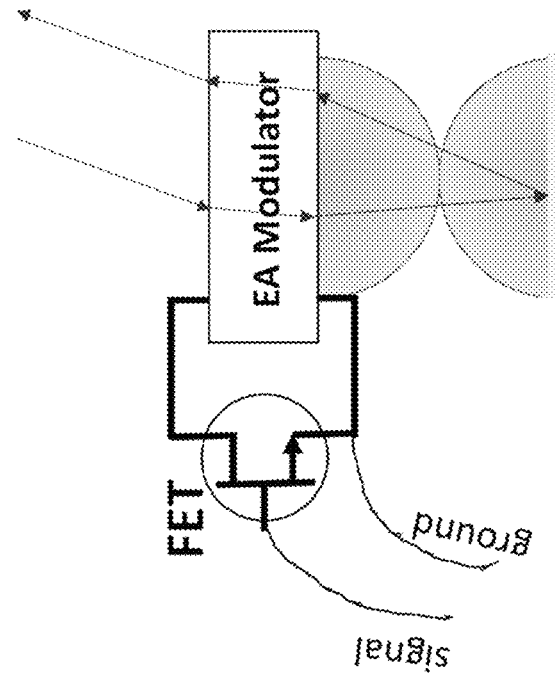
FIG. 3B depicts a transducer in the form of a common source FET configuration in accordance with an illustrative embodiment.
Figure 3A:
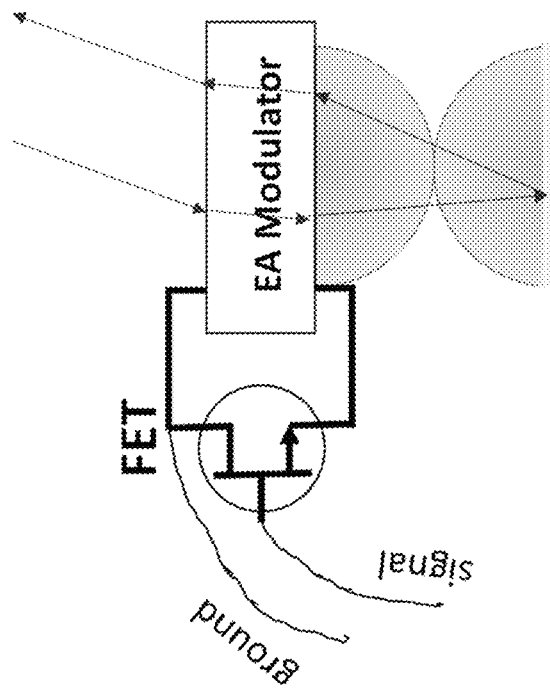
FIG. 3A depicts a transducer in the form of a source-follower field effect transistor (FET) configuration in accordance with an illustrative embodiment.

FIG. 3A depicts a transducer in the form of a source-follower field effect transistor (FET) configuration in accordance with an illustrative embodiment. FIG. 3B depicts a transducer in the form of a common source FET configuration in accordance with an illustrative embodiment. The embodiments of FIG. 3 are for analog data transmission. The FET drain and source of the transistor are connected to the two sides of an electroabsorptive (EA) modulator, and the gate of the FET provides the high impedance voltage read point for the electrical probing of the neural spikes. The EA modulator is made of a p-doped region, and n-doped region, and a multi-quantum well region (MQW). An applied voltage across the modulator can change the electric field inside the MQW region and hence its effective bandgap due to the quantum confined Stark Effect (QCSE). Optical illumination at wavelengths absorbed by MQW produces electron-hole pairs which can then produce an open-circuit voltage across the device if the device terminals are left open. Based on the neural signal on the gate, the transistor produces a variable load in parallel to the modulator and hence changes the effective voltage across the modulator under illumination. This voltage in turn changes the bandgap of the modulator and hence the change of absorption of the beam going through the modulator. The result is that the neural voltage spikes modulates the transmission of light passing through the modulator, and so the neural spikes are encoded on the beam returning back to the interrogator.

The ground wire could be connected to the drain or the source of the transistor to make a source-follower or common-source configuration, as depicted in FIGS. 3A and 3B respectively. These two configurations provide a gain of ~1 for the source-follower configuration and a high gain (depending on the total resistive load of the transistor and modulator, and the transimpedance gain of the transistor) for the common-source configuration. In an illustrative embodiment, the source follower configuration can be used for extra-cellular microprobes and the common source configuration can be used for inter-cellular microprobes.

Figure 3C:
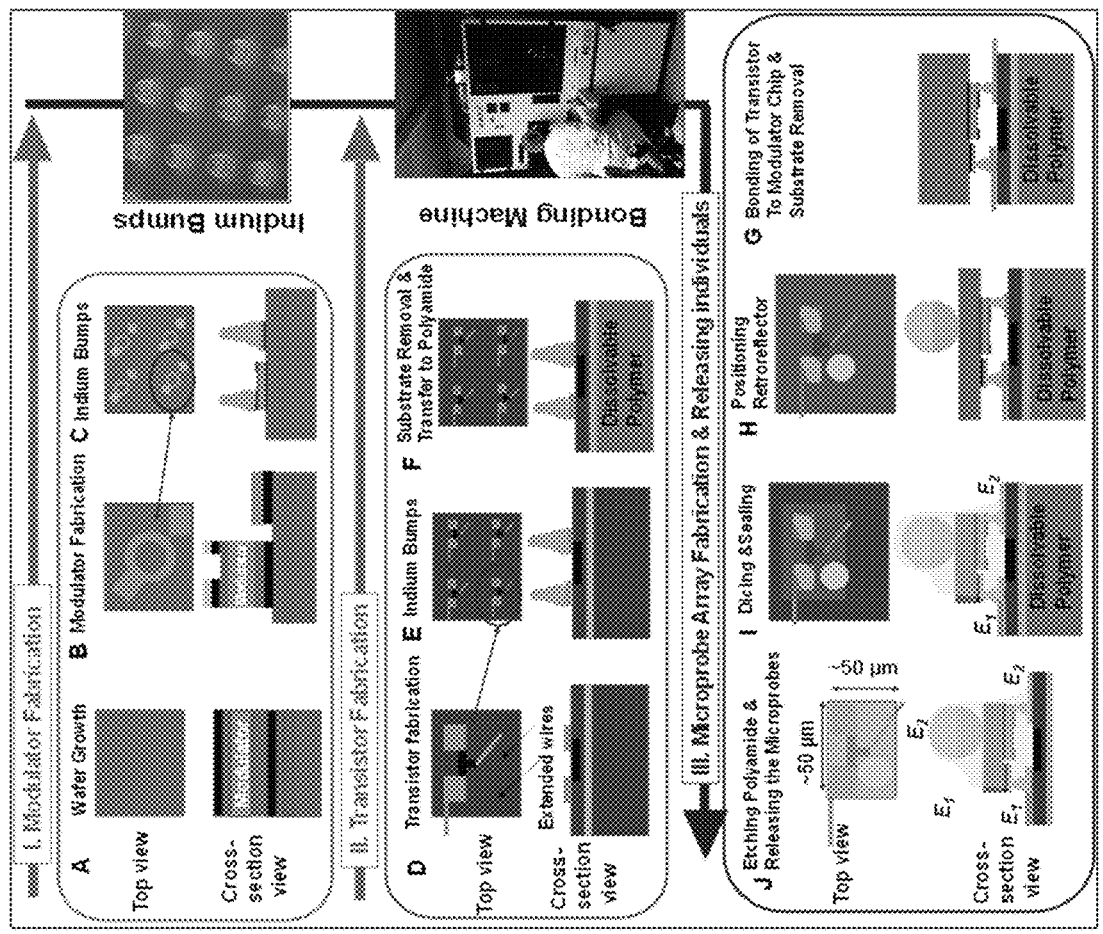
FIG. 3C depicts a process for large-scale fabrication of microprobes in accordance with an illustrative embodiment.

FIG. 3C depicts a process for large-scale fabrication of microprobes in accordance with an illustrative embodiment. The fabrication process has been shown to produce over 75,000 microprobes in a single batch, and this number can be scaled up to millions. The fabrication method is based on high throughput integration of dissimilar micro-components, and involves use of the best bonding and integration tools currently available. For example, in one embodiment, an automated flip-chip bonding machine (e.g., SET FC-150) with ~1 $\mu$m post-bonding accuracy can be used.

Described below are two examples for the interrogator design. The first example is based on conventional coherent reflectometry, such as systems used in coherence optical tomography, combined with conventional bulk optical head. This example only provides one-way data transmission from microprobes to the interrogator (i.e. reading neural signals). The second example of interrogator allows bi-directional data transmission, as well as a thin and flexible optical head, similar to what is depicted in FIG. 1B.

Figure 4:
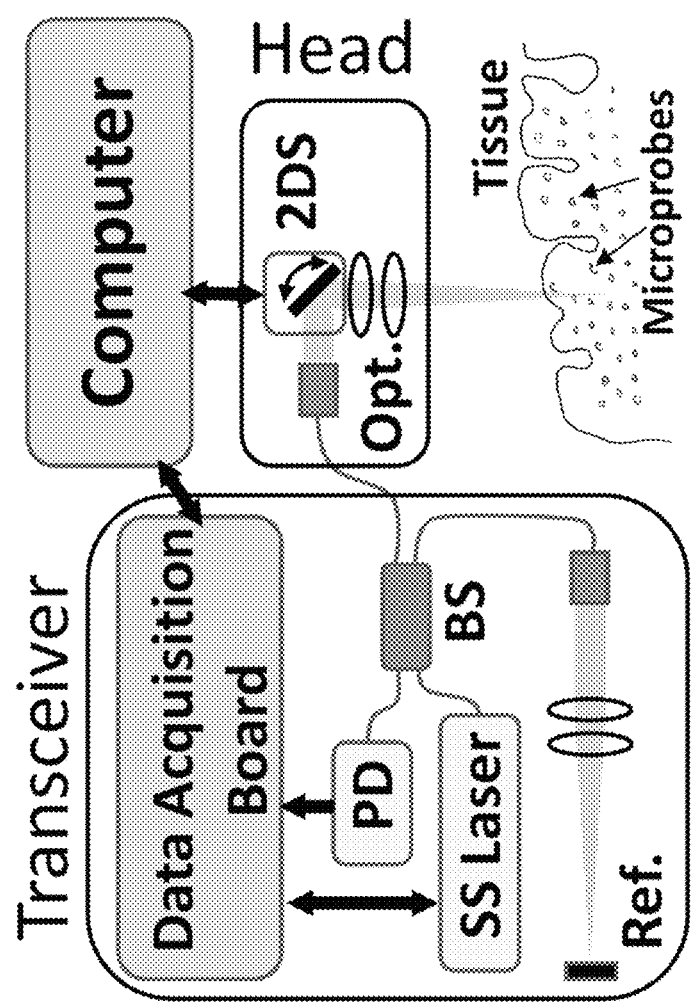
FIG. 4 shows an example of a non-implantable interrogator in accordance with an illustrative embodiment.

In one embodiment, the interrogator is non-implantable and made with conventional parts. FIG. 4 shows an example of a non-implantable interrogator in accordance with an illustrative embodiment. The interrogator is made of a coherent reflectometer which could be similar to an optical coherence tomography system, and a scanning optical head. To read neural signals from the microprobes, the reflectometer measures the reflected power from microprobes that are modulated with the neural signal data. The reflectometer produces a map of reflectivity versus depth, and hence each axial (depth, z) scan can measure multiple microprobes implanted at different depths. The two-dimensional scanner (2DS) located at the optical head then deflects the optical beam to another lateral (x,y) location, where the process is repeated until the area of interest is scanned. It can be assumed that this process takes a time of $T_{scan}$, and is finished at time intervals $T_1, T_2, \ldots T_K$. Each completed scan produces a snapshot of all signals versus their 3D locations (x,y,z). The signal from the n-th microprobe located at $(x_n, y_n, z_n)$ can then be reconstructed at sampling times $T_1, T_2, \ldots T_K$, and with a timing resolution (latency) of $T_{scan}$.

As also shown in FIG. 4, the transceiver of the interrogator includes a data acquisition board that interfaces with a computer. Any type of data acquisition board known in the art may be used. The interrogator also includes a reference reflector (Ref), a photodiode (PD) and a swept source laser (SS Laser) that interface with the data acquisition board. A beam-splitter (BS) receives light from the SS Laser and passes the light to the optical head. The optical head, which also can interface with the computer, includes the two-dimensional scanner (2DS) and optics to receive and direct the received light from the SS Laser.

In another embodiment, the system can utilize an implantable interrogator with a thin optical head and a transceiver system. In such an embodiment, the optical head is implanted under the skull, and communicates with the transceiver system via a single optical fiber (i.e. similar to the embodiment of FIG. 1B and FIG. 2). In an illustrative embodiment, the thin optical head can be an all-passive and an all-optical system. These features are important, since being all passive ensures negligible heat generation, while being all-optical makes it possible to connect the optical head to the transceiver via a single flexible fiber strand.

Figure 5:
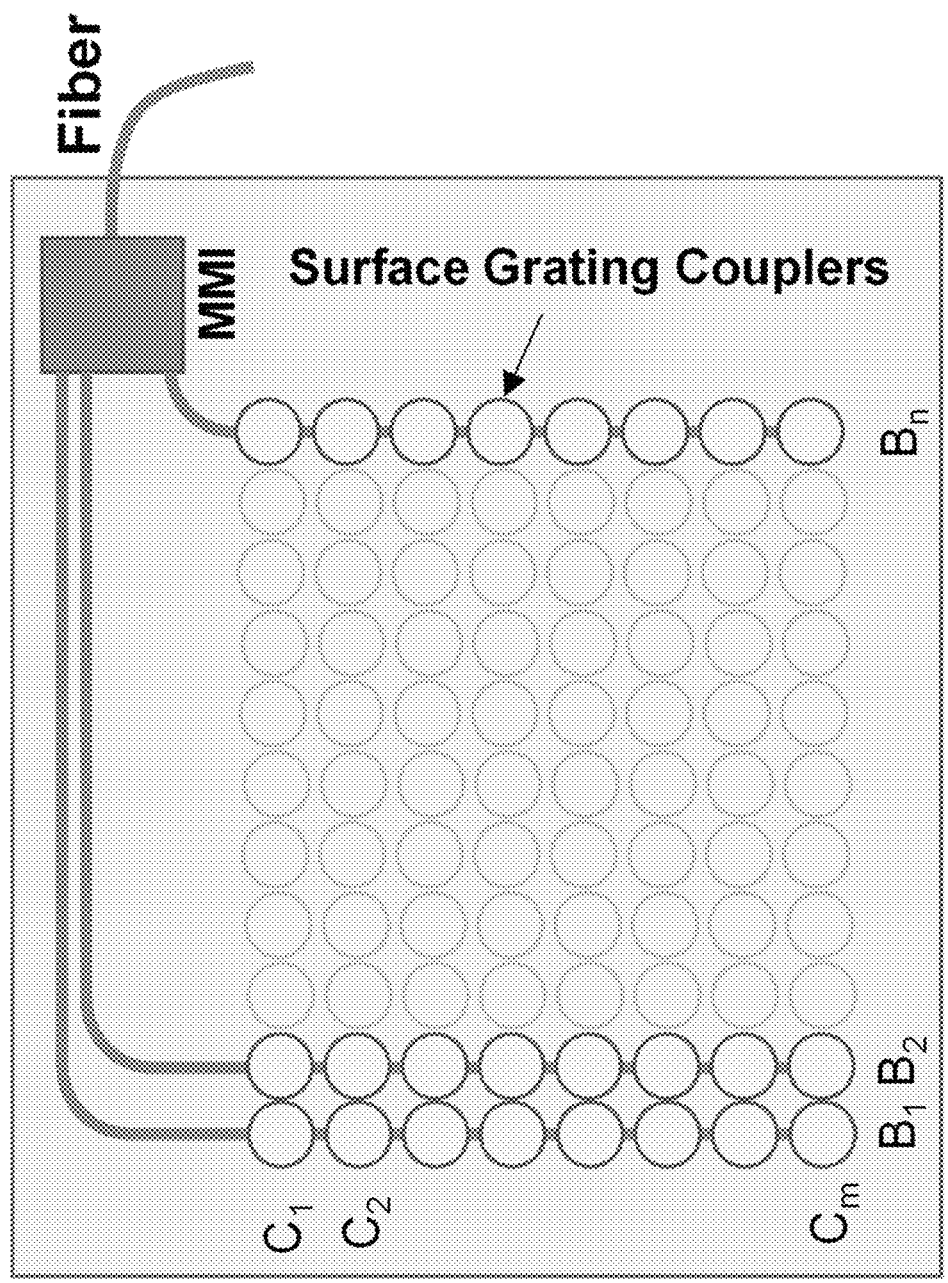
FIG. 5 depicts an implantable optical head design in accordance with an illustrative embodiment.

FIG. 5 depicts an implantable optical head design in accordance with an illustrative embodiment. More specifically, FIG. 5 is an example of an all-passive optical head with n×m surface grating couplers and a multi-mode interference (MMI) coupler, in which a single optical fiber connects the optical head to the transceiver. The optical head involves n waveguide bands, and m optical wavelength channels. The optical head also includes the in-plane multi-mode interference coupler dividing the input light to $B_1, B_2, \ldots B_n$ bands, and an array of surface grating couplers. The output of each band is fed to in-plane surface grating waveguides. Each section of the waveguide couples one of the $C_1, C_2, \ldots C_m$ channels out of the plane. As the input wavelength is swept, the optical head spatially separates the wavelengths into small sections of the overall area. The signals sent to, and received from, the neural microprobes are modulated and demodulated in the modulation/demodulation system described below.

Figure 6:
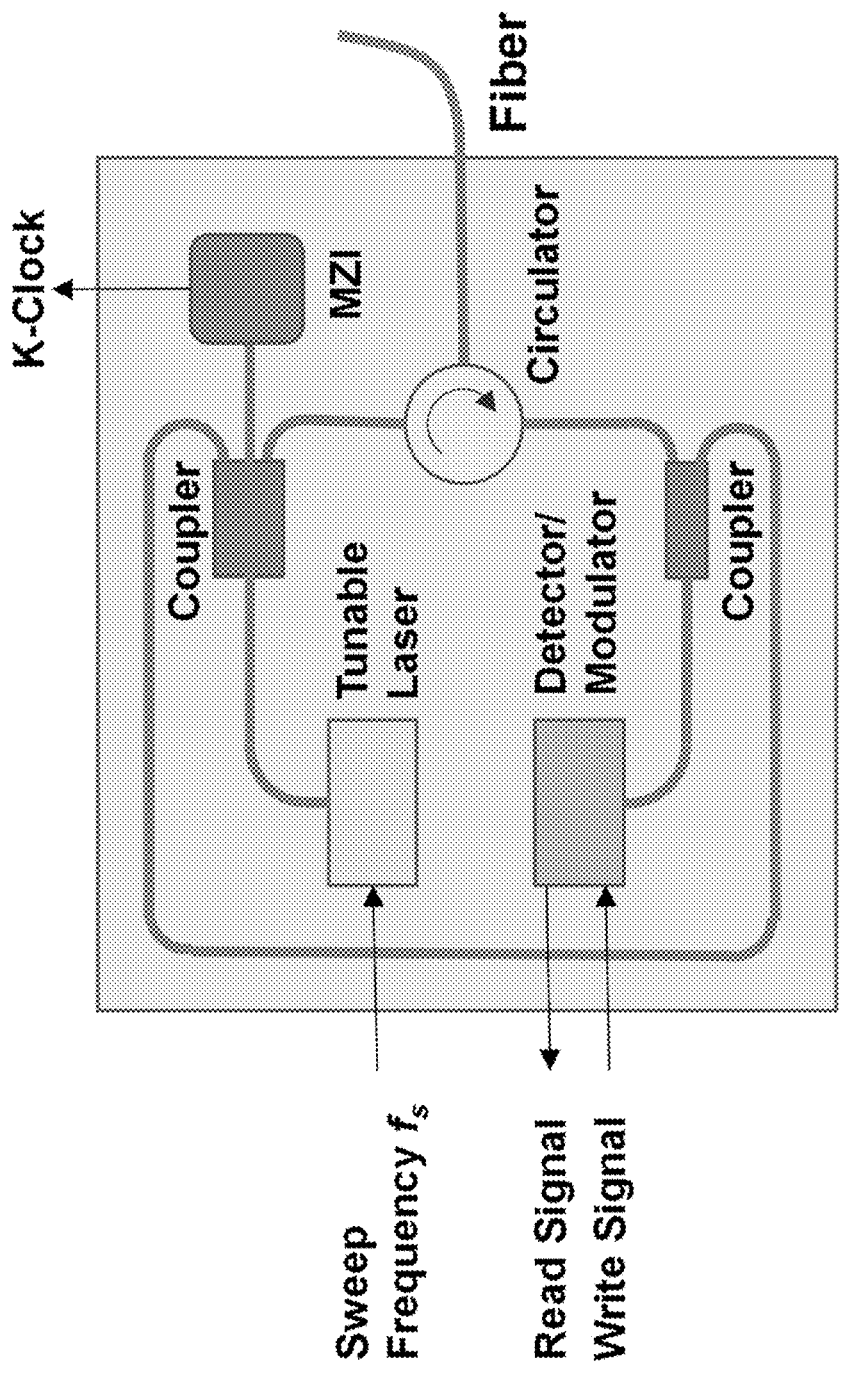
FIG. 6 depicts a transceiver for an implantable system in accordance with an illustrative embodiment.
Figure 7:
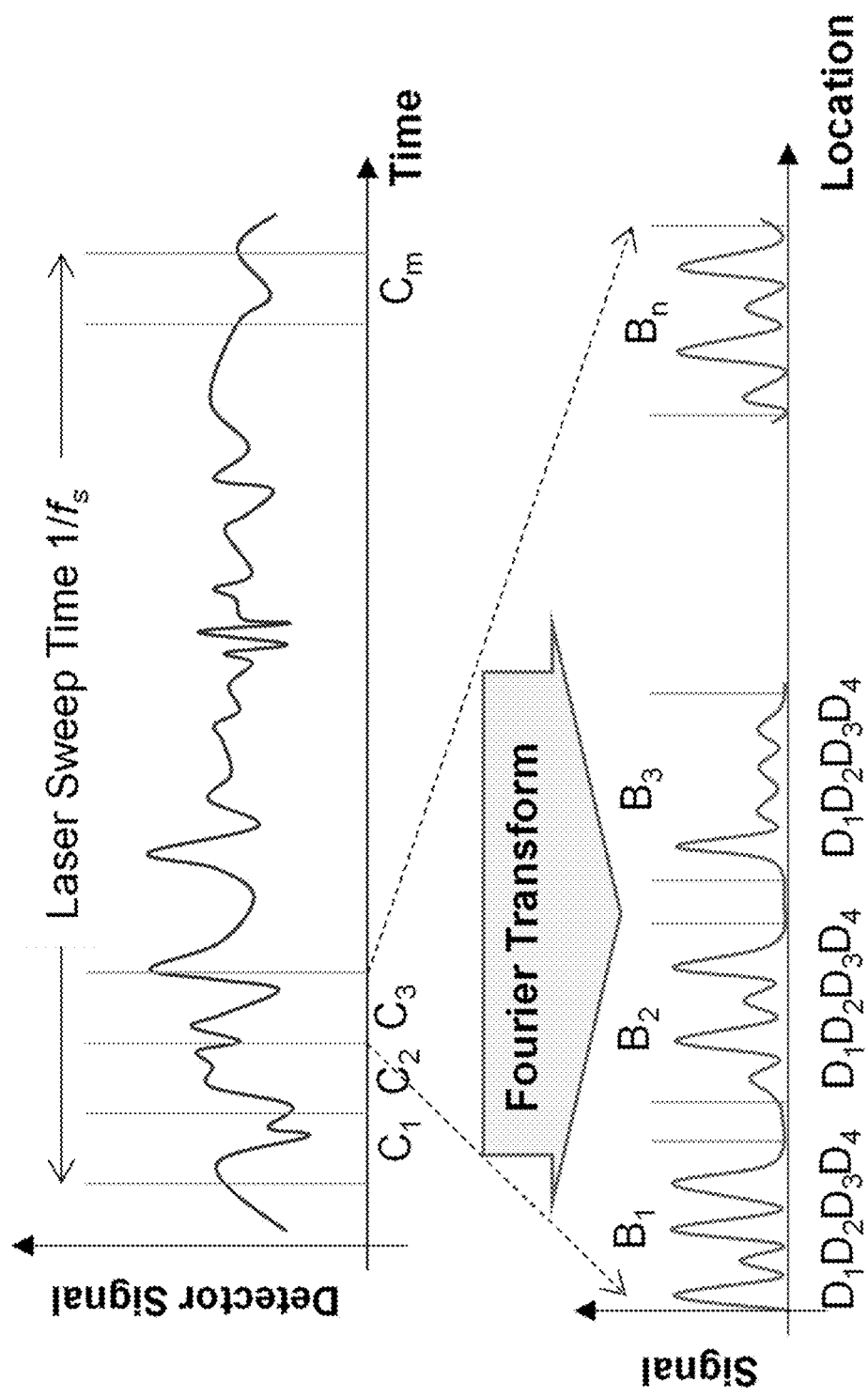
FIG. 7 depicts a raw detector signal (top) and the fast Fourier transform (FFT) of a particular wavelength channel $C_3$, showing different bands $B_1$, $B_2$, etc. and different depth, $D_1$, $D_2$, etc. in accordance with an illustrative embodiment.

FIG. 6 depicts a transceiver for an implantable system in accordance with an illustrative embodiment. In such an implantable system, the transceiver system can be located above the skull. The main optical components of the transceiver system are a tunable laser diode, waveguide couplers, an EA modulator/detector, a Mach-Zehnder interferometer (MZI), a K-clock, and a circulator. The transceiver system can also include additional components, such as a frequency generator and a data acquisition system for interfacing between analog and digital data. In an illustrative embodiment, the output of the detector includes all data from the neural microprobes in the Fourier domain. FIG. 7 is a diagram that depicts a coded signal sequence using an implantable neural sensing system in accordance with an illustrative embodiment. FIG. 7 depicts a raw detector signal (top) and the fast Fourier transform (FFT) of a particular wavelength channel $C_3$, showing different bands $B_1, B_2$, etc. and different depth, $D_1, D_2$, etc.

In an illustrative embodiment, the light reflected by the retroreflector is modulated by the analog/digital signal and returns back to the transceiver system of FIG. 6 to be decoded. The neural stimulation 'write' signal is sent via the same hardware to the neural microprobes, since the detector in the transceiver system has a complete topological symmetry with respect to the aforementioned neural microprobes (i.e. the type provided in the example neural microprobes described herein). The detector in the transceiver system can be an electroabsorption modulator that in the 'read' mode (i.e. reading neural signals) is biased to absorb light and produce the 'read' signal. In the write mode (i.e. stimulation), the write signal modulates this device with the time/wavelength sequence that corresponds to each microprobe, as shown in FIG. 7. As an example of stimulation, the system may write to (i.e., stimulate) one or more neurons using light transmitted from the optical head to determine a response of the one or more neurons and/or a response of neurons in other areas of the brain. Such a write process has numerous applications, such as mapping the relationship between areas of the brain, implementing mind control (both sensory and motor) for prosthetics, etc. The system is therefore capable of acting as a bidirectional neural communication system.

It is noted that the time/wavelength specific to each microprobe is already produced in the previous read cycle, and hence is insensitive to the slow variation of the microprobe location (compared with the KHz read/write speed). Conversely, the modulator in each microprobe is biased in the read mode to only absorb the incident light and hence becomes a photodetector. The generated photocurrent in this photodetector is proportional to the light intensity, and hence directly reproduces the digital write signal coded by the transceiver system. The signal is then decoded by an application specific integrated circuit (ASIC) chip in a digital system, or directly used in an analog system, to produce the stimulation analog signal.

Various system parameters of the proposed neural sensing system include total laser power ($P_L$), tuning range of the laser ($\Delta_L$), sweep rate of the laser ($f_s$), diameter of the neural microprobes ($d_n$), read data bandwidth for each neural microprobe ($BW_n$), maximum implant depth ($D_n$), area of implant coverage ($A_n$), average distance between neural microprobes ($L_n$), total number of surface grating outcouplers ($N_{gr}$), total number of neural microprobes ($N_n = A_n D_n / L_n^3$), number of wavelength channels ($N_{ch}$), and channel optical bandwidth ($BW_{ch}$).

The total bandwidth of each channel is related to the neural microprobe spacing $L_n$ by: $BW_{ch} := 2 \cdot \ln(2) / \pi \cdot \lambda_0^2 / L_n \cdot n_B$, where $\lambda_0$ is the center laser wavelength, and $n_B$ is the refractive index of the tissue. The number of wavelength channels is then $N_{ch} = \Delta_L / BW_{ch}$. The number of bands within the optical head can also be calculated, as their optical pathlength should be larger than the optical pathlength of the implant depth: $N_B := A_n^{0.5} \cdot n_{WG} / D_n \cdot n_B$, where $n_{WG}$ is the optical index of the waveguide. Finally, the number of depth points resolved is simply depth divided by depth resolution, or $N_d = D_n / L_n$. The total number of the spatially resolvable points with this method is the product of the three, or $N_r = N_{ch} N_B N_d$. It follows that the sweeping frequency of the laser is the bandwidth of each spatially resolvable point times the number of the spatial point $f_s = N_r BW_n$ The sensitivity of the coherent detection based on swept-source method can readily achieve shot-noise limit, which is typically in the order of ~100 dB. One can also calculate the signal-noise ratio (SNR) from the sensitivity and the optical loss in the link. The main sources of loss considered in experimental models are from the MMI splitter, the waveguide loss, implanted microprobe+brain tissue loss, and the neural microprobe's optical fill-factor—all of which are calculable based on experimental data and other data known in the art.

The difference between the sensitivity and the two-way total insertion loss is the SNR (all in dB). Once the SNR is known one can calculate the channel bitrate in a digital communication, depending on the modulation method. Bit error rate (BER) will also be calculable from the SNR and modulation method. In a purely analog mode, the SNR is simply the SNR of the signal before it is digitized in the transceiver.

The experimental and the calculated return loss obtained in experiments sets the basis for evaluating the performance metrics of the proposed system. Particularly, an evaluation is made of the maximum number of microprobes that can communicate with an interrogator based on the implantation depth, the overall signal SNR, and the sampling rate per microprobe. While digital communication between microprobes and the interrogator is possible, and potentially offers a far better information channel capacity than analog communication, evaluating such systems would strongly depend on the choice of the many digital coding and compression methods. Therefore, a focus of the experiments was on analog communication. For analog communication, the optical beam returning from the microprobe is proportional to the neural signal. The modulated optical signal is attenuated within the tissue before reaching the optical detection system. The electrodes of the microprobe could either sense the voltage inside (intracellular) the neurons or at the vicinity of them (extracellular). The use of an integrated electronic amplifier can be included in the system for detecting the extracellular voltages since they are typically 100 times smaller than their intracellular counterparts. Neglecting the limitation of the lateral beam scan rate, the constraint on the number of microprobes ($N_n$) originates from the limited power normalized sensitivity bandwidth product ($S_n \cdot B_{sys}$) of the homodyne optical interrogator, as follows:

$$N_n(z, d) < S_n \cdot B_{sys} \cdot \frac{\alpha_m \cdot L_R(z, d) \cdot P_s(z)}{B_m \cdot SNR_m}, \qquad \text{Eq. 1}$$

where $S_n$ is the sensitivity of the system divided by the light source power, $SNR_m$ is the required signal to noise power ratio, and $B_m$ is the required bandwidth for reliable recording of action potentials. $\alpha_m$ is the modulation depth of the optical modulator, $L_R$ is the return loss at the depth z and from retroreflectors with diameter d, and $P_s$ is the maximum allowed illumination power, which depends on the depth of implantation z.

This calculation shows that for the experimental data obtained, and the reported sensitivity and bandwidth of the reflectometer, assuming a communication bandwidth of 1 kHz between the interrogator and each microprobe, and a minimum $SNR_m=9$, one interrogator can read more than 100,000 microprobes at a depth exceeding 200 μm. Better interrogator and microprobe technologies can significantly enhance this performance in the future.

The maximum number of neurons that can be recorded simultaneously n can be calculated for a recording bandwidth per neuron $B_m$ and a signal-to-noise ratio $SNR_m$. This model is based on a simple lens solution without adaptive optics. The maximum number of neurons n that can be recorded simultaneously is represented by the relation below in which $L_R$ is returned signal strength, $P_s$ is laser power, and $\alpha_m$.

$$n < \frac{\alpha}{2qB_m SNR_m} L_R \alpha_m P_s; \alpha = qn/h\nu \qquad \text{Eq. 2}$$

Experiments were conducted to validate of a strong retroreflector return signal through brain tissue. Widely available microsphere products were used to conduct the experiments. These microspheres can be chemically produced in mass numbers with a relatively low cost. The microspheres were half-coated with gold. As shown in the SEM images of FIG. 8, high-quality microsphere retroreflectors with ~50 μm diameter were generated and used for the experiments. In order to be highly reflective, it was determined that the thickness of the gold should be 150 nm or greater. FIG. 8A is a high magnification image of a retroreflector half-coated with metal in accordance with an illustrative embodiment. FIG. 8B depicts the reflection of a visible laser (with a wavelength of 850 nm) from an island of microsphere retroreflectors in accordance with an illustrative embodiment. FIG. 8C is an optical image of a large number of sphere retroreflectors produced in accordance with an illustrative embodiment. FIG. 8D depicts the retroreflection of a 1550 nm laser from a sphere retroreflector buried under a 300 μm brain slice in accordance with an illustrative embodiment.

Figures 9A, 9B:
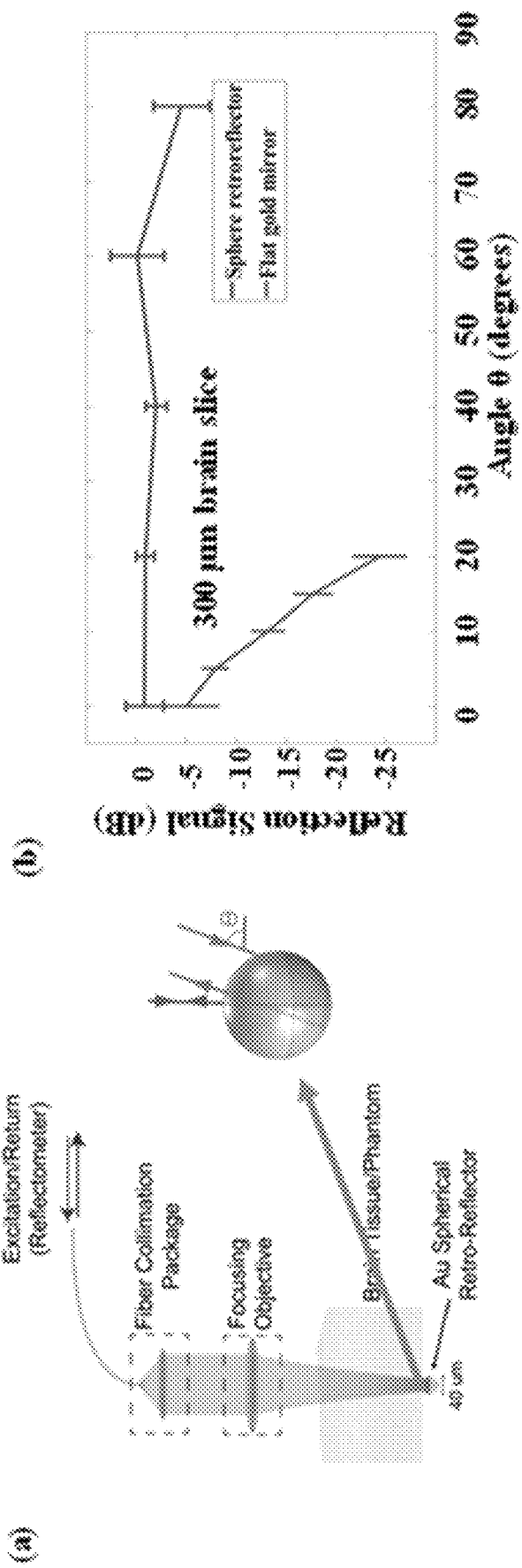
FIG. 9A depicts a schematic of an in-vitro experiment in accordance with an illustrative embodiment.
FIG. 9B depicts the angular dependency of the reflection when a 50 μm sphere retroreflector and a flat gold mirror (of the same size) are used in accordance with an illustrative embodiment.

FIG. 9A depicts a schematic of an in-vitro experiment in accordance with an illustrative embodiment. As shown, the schematic includes a spherical retroreflector embedded in brain tissue, a focusing objective, a fiber collimation package, and an excitation/return reflectometer. The diameter of the microsphere retro-reflector was ~50 μm throughout the experiments. In alternative embodiments, a different diameter can be used, such as 2 μm, 5 μm, 10 μm, 20 μm, 30 μm, 40 μm, 60 μm, etc. To examine the angular sensitivity of the retroreflector, it was placed underneath a brain phantom (thickness of ~300 μm) and the reflection was measured while changing the tilt angle of the incident infrared (IR) beam at wavelength of 1550 nm.

Figures 9C, 9D:
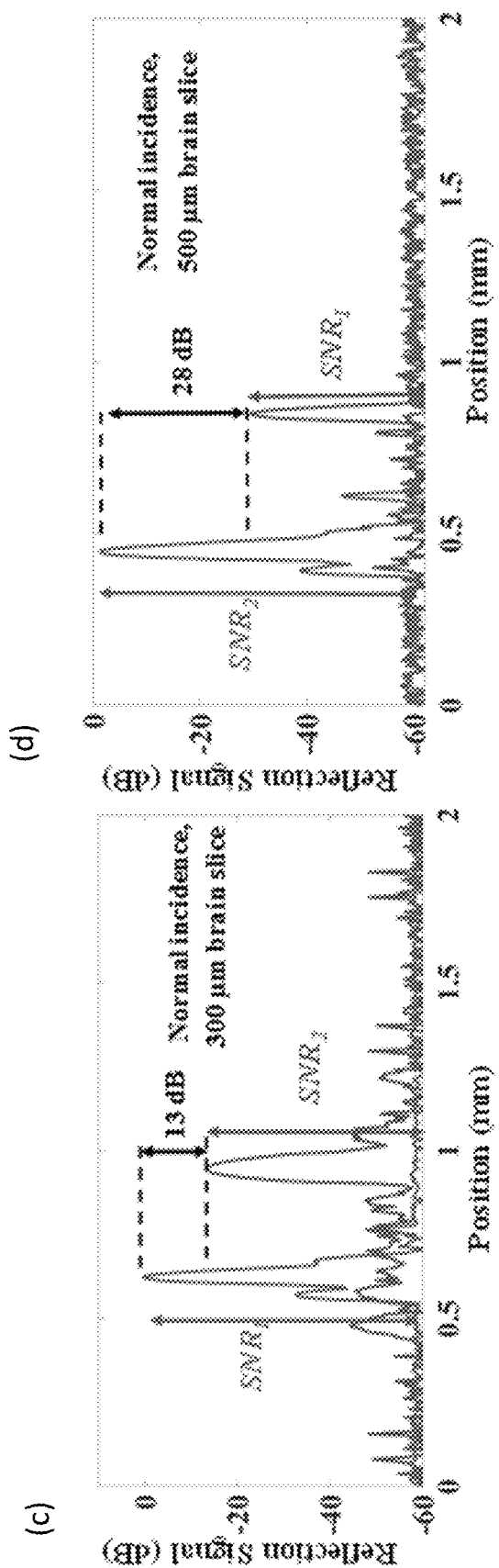
FIG. 9C depicts a depth profile of the reflection versus depth for brain slice thickness of 300 μm in accordance with an illustrative embodiment.
FIG. 9D depicts a depth profile of the reflection versus depth for brain slice thickness of 300 μm in accordance with an illustrative embodiment.
Figure 9E:
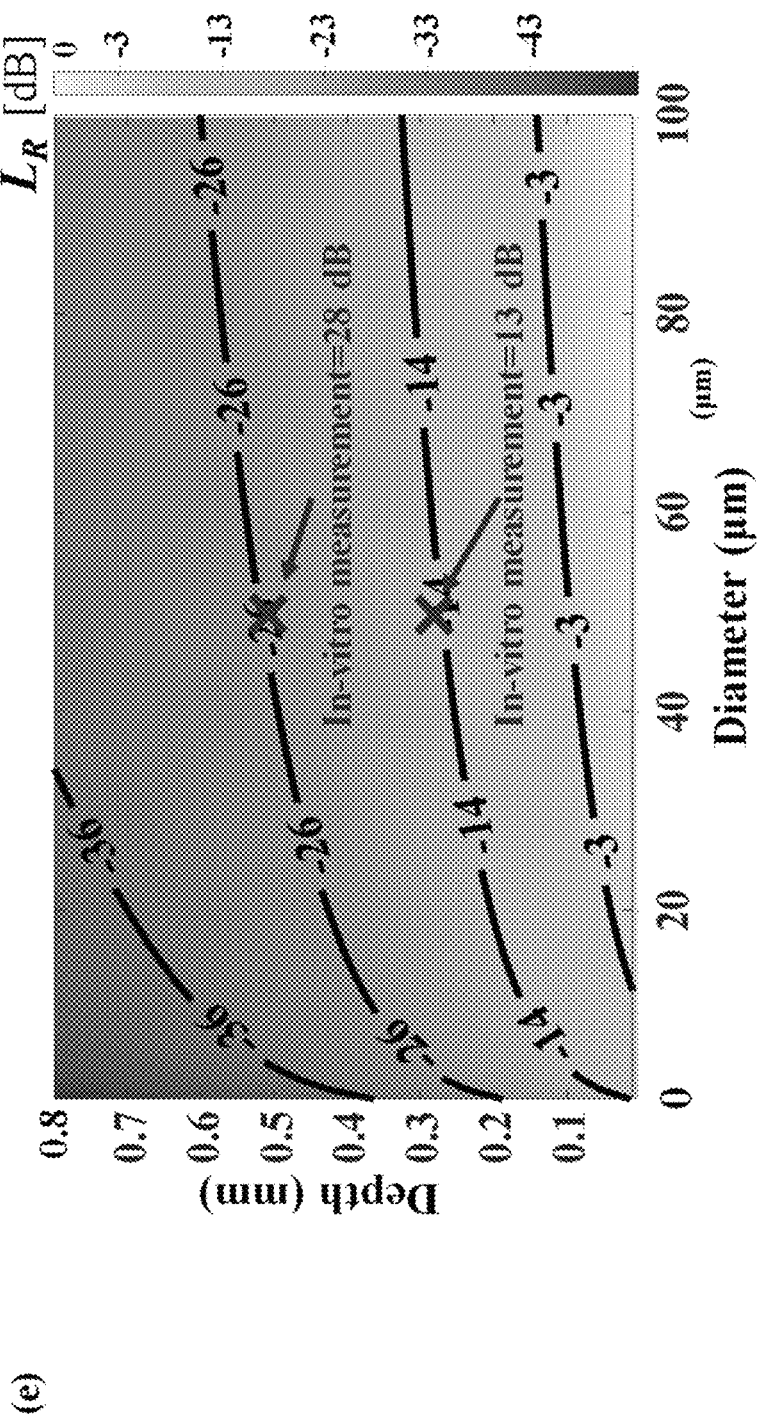
FIG. 9E is a graph indicating that the experimental return loss values show excellent agreement to simulation results in accordance with an illustrative embodiment.

The above-described experiment was also repeated using a flat gold mirror instead of a spherical retroreflector. FIG. 9B depicts the angular dependency of the reflection when a 50 μm sphere retroreflector and a flat gold mirror (of the same size) are used in accordance with an illustrative embodiment. A 300 μm brain slice covered the reflectors in these experiments. It is evident that the microsphere retroreflector is superior to the flat gold mirror (at any angle) for having less sensitive reflection with mis-orientation. The microsphere retroreflector can therefore operate at an extremely large tilt angle of ±80 degrees, with a small loss. FIG. 9C depicts a depth profile of the reflection versus depth for brain slice thickness of 300 μm in accordance with an illustrative embodiment. FIG. 9D depicts a depth profile of the reflection versus depth for brain slice thickness of 300 μm in accordance with an illustrative embodiment. By removing the slices and comparing the magnitude of the reflection, the return loss was estimated to be 13 dB and 28 dB due to the presence of the 300 μm and 500 μm brain tissue, respectively. FIG. 9E is a graph indicating that the experimental return loss values show excellent agreement to simulation results in accordance with an illustrative embodiment. Specifically, the reflection with and without the brain slices (as shown in FIGS. 9C and 9D) were measured and the return loss was deduced in each case, which matched with the modeling results shown in FIG. 9E.

Experimental validation of the entire system was also performed. To validate the system, an experiment was performed using a home-built reflectometer (transceiver), and conventional optics such as an objective lens (optical head). The microprobe was made with an optical modulator and a field effect transistor, as described herein, and placed underneath the brain phantom to measure the SNR when recording an action potential (AP) signal using the proposed setup. The optical modulator had an optical bandwidth of 70 nm and a modulation depth of 16% per one volt change of its input voltage.

Figure 10A:
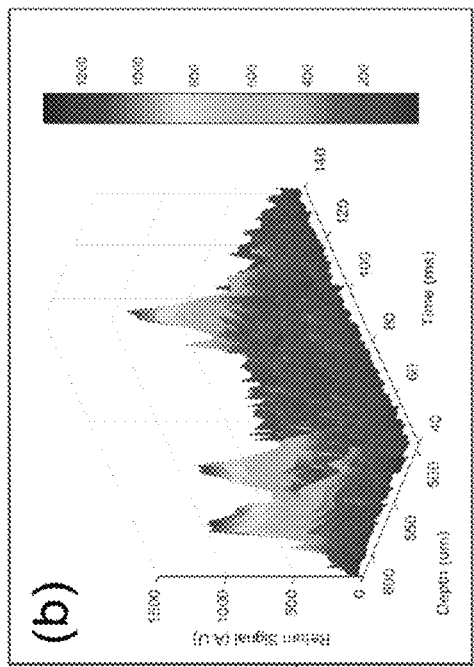
FIG. 10A depicts the train of action potentials generated by the optical modulator and captured by the interrogator system in accordance with an illustrative embodiment.
Figure 10B:
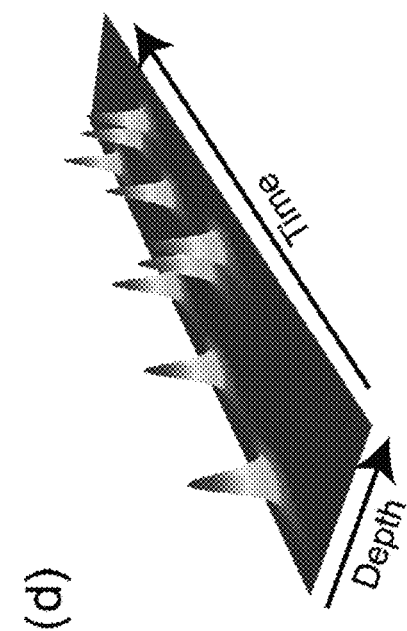
FIG. 10B depicts the measurement with the presence of a 300 μm brain phantom between the modulator and the interrogator in accordance with an illustrative embodiment.
Figure 10C:
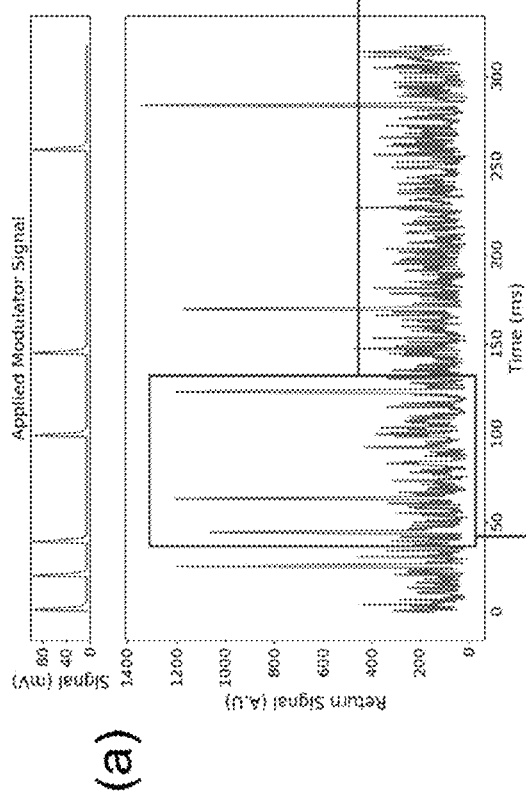
FIG. 10C depicts a zoomed in spatio-temporal view of the temporal response in accordance with an illustrative embodiment.
Figure 10D:
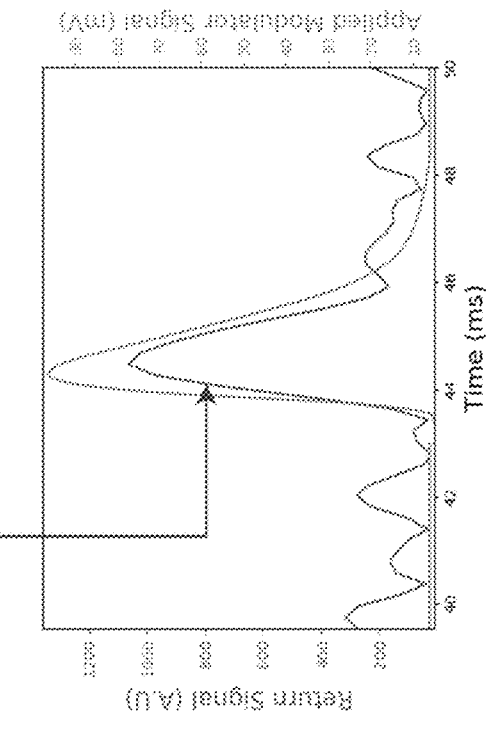
FIG. 10D depicts an extended view of the temporal response in accordance with an illustrative embodiment.

The incident optical power was ~1.6 μW and the spot size was ~45 μm, which results in a maximum intensity of 0.8 $mW/mm^2$ on the tissue, which is within the accepted safe power level of 1 $mW/mm^2$ according to ANSI Z136 standard. FIG. 10A depicts the train of action potentials generated by the optical modulator and captured by the interrogator system in accordance with an illustrative embodiment. In FIG. 10A, the measurements depicted are real time optical measurement of neural pulse train through a 300 μm brain phantom. The upper trace of FIG. 10A shows the signal applied to the modulator (0 to 98.9 mV). FIG. 10B depicts the measurement with the presence of a 300 μm brain phantom between the modulator and the interrogator in accordance with an illustrative embodiment. The spatio-temporal data collected by the interrogator was at a sampling rate of 4878 Hz and a depth resolution of 45 μm. FIG. 10C depicts a zoomed in spatio-temporal view of the temporal response in accordance with an illustrative embodiment. FIG. 10D depicts an extended view of the temporal response in accordance with an illustrative embodiment. A compilation of similar measurements with different depth of the modulator, as shown in FIG. 10D, demonstrates the proposed functionality of this system to track many microprobes accurately in both the time and space domain. This approach can also be used with multiple microprobes, implanted at different depths, to produce a spatio-temporal data map of the nearby neural activities.

Figure 11A:
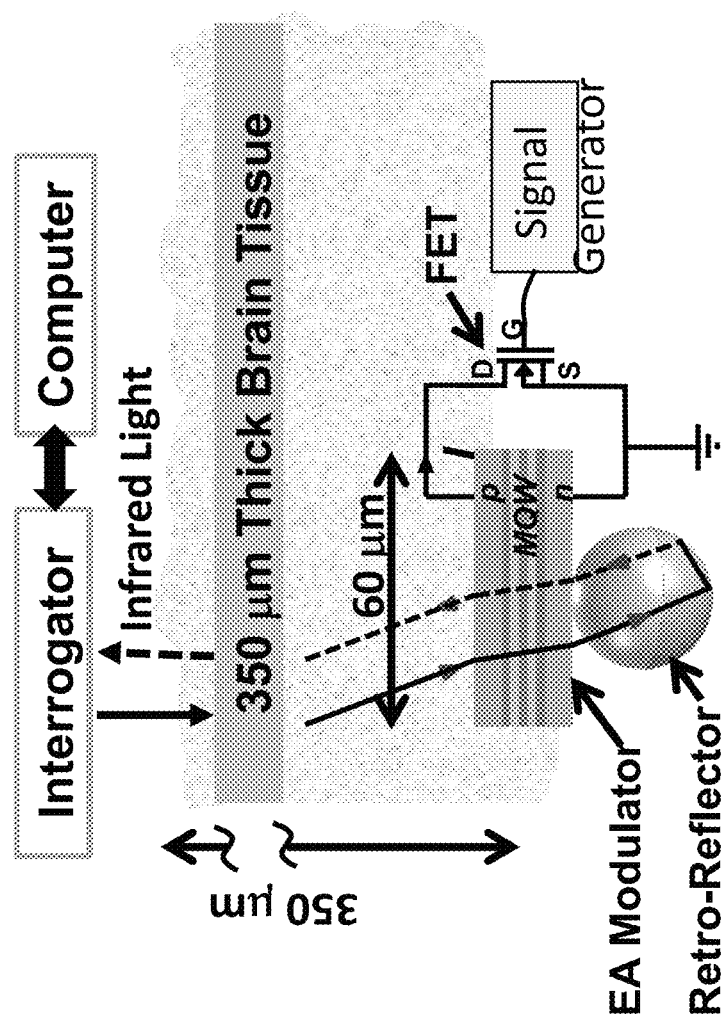
FIG. 11A is a diagram of an in-vitro experiment performed in accordance with an illustrative embodiment.
Figure 11B:
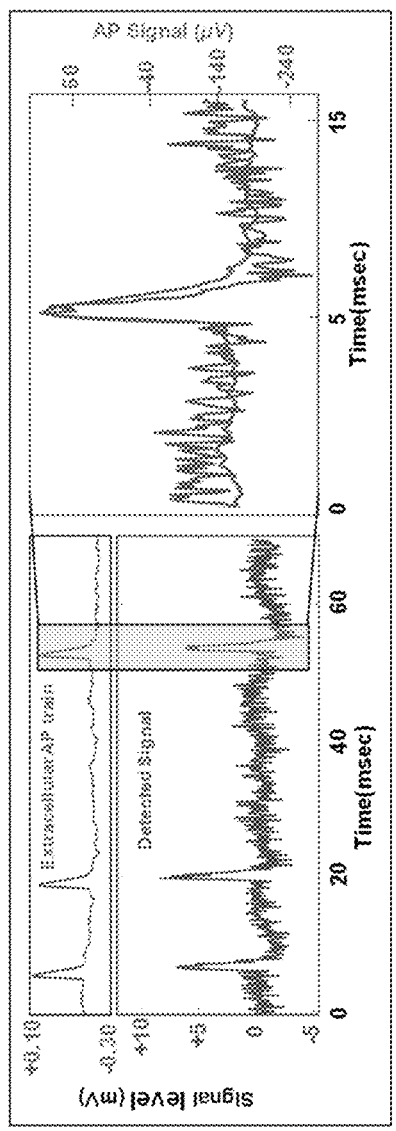
FIG. 11B depicts computer-generated results of the in-vitro experiment depicted in FIG. 11A in accordance with an illustrative embodiment.

FIG. 11A is a diagram of an in-vitro experiment performed in accordance with an illustrative embodiment. FIG. 11B depicts computer-generated results of the in-vitro experiment depicted in FIG. 11A in accordance with an illustrative embodiment. The experiment was conducted with a 60 μm self-powered microprobe that transmits signals of ~100 μV through 350 μm of brain tissue with a SNR of ~9. The total incident optical power was only 150 μW, and the optical probing and powering pulse was as short as ~1 nanosecond. The interrogator was able to communicated with 500,000 microprobes in 0.5 milliseconds, and there was no interference with optogenetic wavelengths. An in-vivo experiment was also conducted with an implanted retro-reflector at 500 μm deep inside of an awake mouse brain. The in-vivo experiment showed excellent agreement to in-vitro results. Additionally, two-photon microscopy images of neighboring neurons shows no observable negative effect on their livelihood.

Figure 12A:
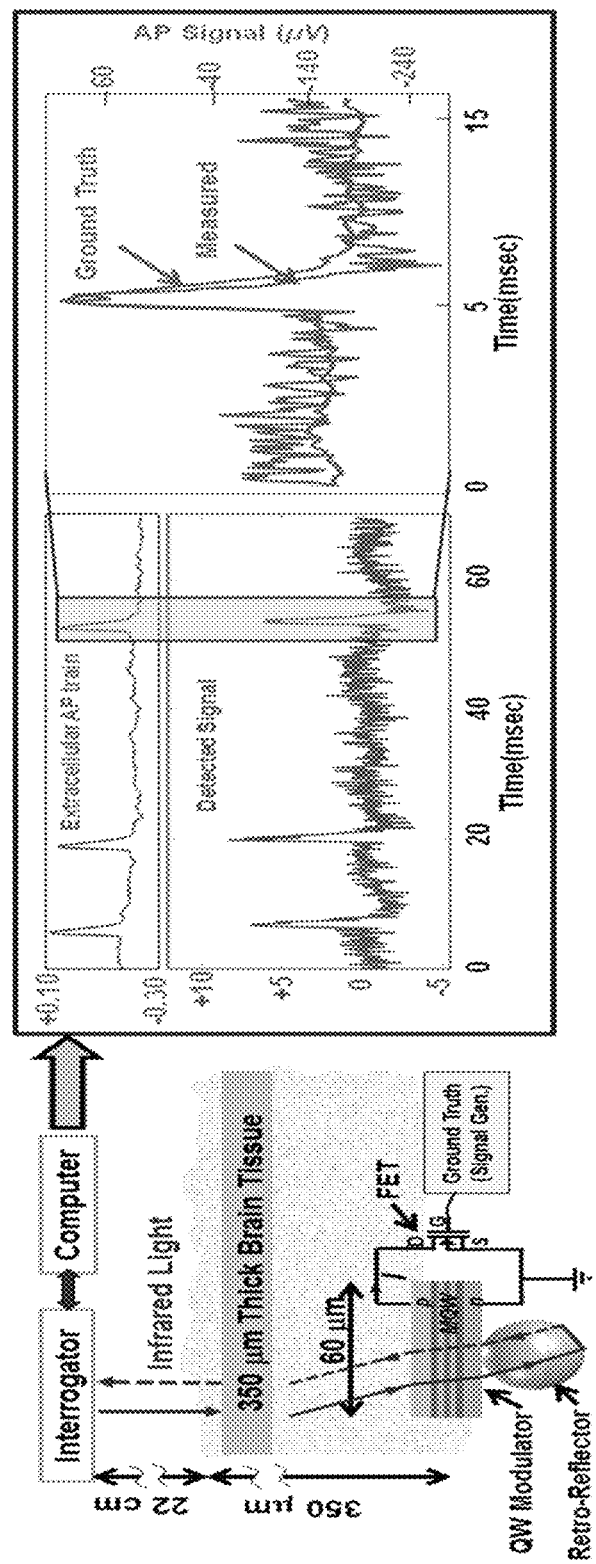
FIG. 12A depicts an experimental demonstration of the proposed system in accordance with an illustrative embodiment.
Figures 12B, 12C, 12D:
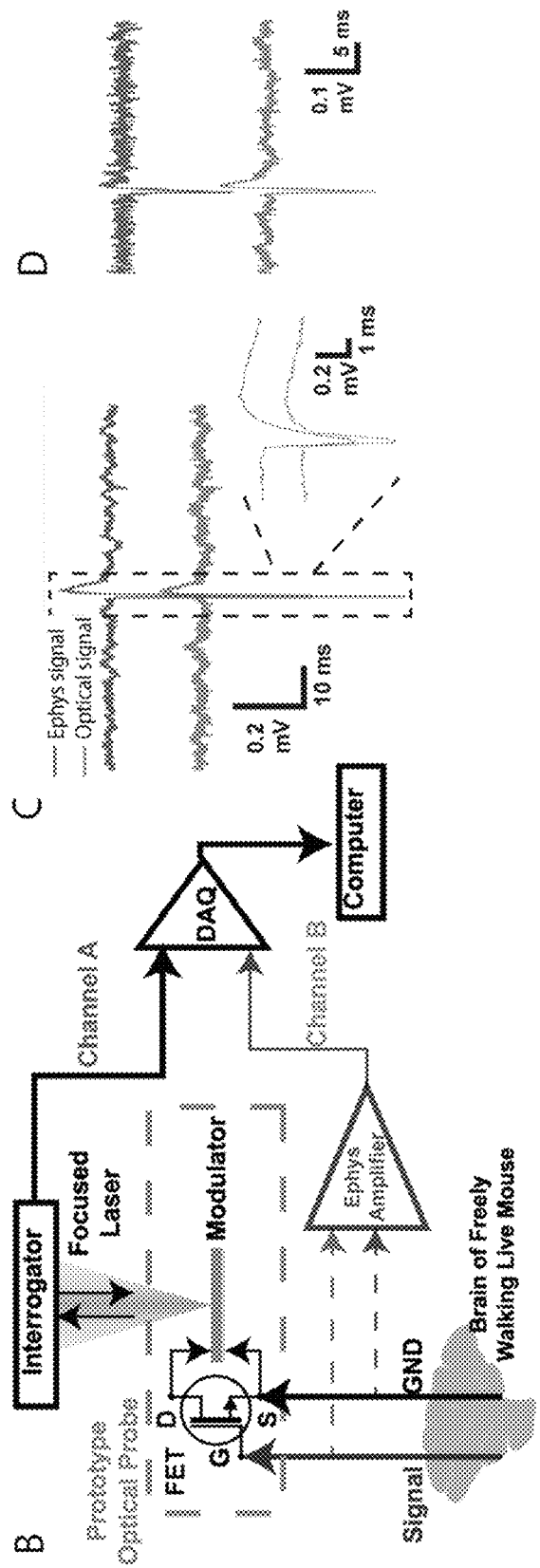
FIG. 12B depicts another experimental demonstration of the proposed system in accordance with an illustrative embodiment.
FIG. 12C depicts example spikes recorded from a first unit in accordance with an illustrative embodiment.
FIG. 12D depicts examples spikes recorded from a second unit in accordance with an illustrative embodiment.

FIG. 12A depicts an experimental demonstration of the proposed system in accordance with an illustrative embodiment. In FIG. 12A, a voltage mimicking an extracellular spike is applied to the gate in-vitro. An input signal is applied to the transistor, and an output signal is decoded from the back-reflected optical beam. In this experiment, the retro reflector was buried under a 350 μm brain slice. The microprobe assembly was completely powered by the infrared beam with incident power of 150 μW. FIG. 12B depicts another experimental demonstration of the proposed system in accordance with an illustrative embodiment. Extracellular spikes were recorded from the hippocampus of an awake mouse walking on a treadmill in accordance with an illustrative embodiment. Example spike recordings were made with a prototype device (external to brain) connected to an implanted ~5 Mohm electrode and ground wire, and the device is again completely self-powered. A standard extracellular amplifier was also connected to the electrode and ground. FIG. 12C depicts example spikes recorded from a first unit in accordance with an illustrative embodiment. FIG. 12D depicts examples spikes recorded from a second unit in accordance with an illustrative embodiment.

As shown in FIG. 12A, the homodyne detection system was able to detect the APs well when the device was covered by a 350 μm brain slice. In the separate experiment of FIGS. 12B-12D, a single FET and surface normal modulator were connected to an extracellular recording electrode (~5 Mohm) and ground wire inserted into the CA1 region of the hippocampus of an awake mouse walking on a treadmill. Extracellular spikes were recorded (with a prototype device and simultaneously with a standard extracellular amplifier for comparison). In both experiments in FIG. 12, the transistor was powered by the modulator absorbing the interrogator infrared light, with an incident power of ~150 μW. A total system noise ~30-40 μV was achieved, resulting in an SNR of >8, despite the fact that the components and the interrogator were not optimized. The experiments in FIG. 12 therefore demonstrate that the core technologies of the approaches described herein are capable of recording extracellular action potentials in a behaving mouse through brain tissue. The model also shows that an optimized system should produce an input-referred noise of a few μV.

Any of the operations described herein can be implemented in the form of computer-readable instructions that are stored on a tangible computer-readable medium and executable by a processing component. For example, the system can utilize a computer that includes a memory which stores the computer-readable instructions, a processor which executes the stored computer-readable instructions, a transceiver that communicates with the neural sensing system and/or other computing devices, and an interface that allows a user to interact with and control the computer.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A neural communication system comprising:
an interrogator that includes an optical head, wherein the optical head transmits a light signal; and
a microprobe configured to contact tissue, wherein the microprobe includes:
a sensor that contacts the tissue;
a transducer that receives the light signal and neural signal information sensed from the tissue by the sensor, wherein the transducer modulates the light signal with the neural signal information; and
a self-powered retroreflector configured to reflect the modulated light signal back to the optical head of the interrogator, wherein a diameter of the microprobe is smaller than 100 micrometers.

2. The neural communication system of claim 1, wherein the interrogator further comprises a transceiver configured to communicate with a computing device.

3. The neural communication system of claim 2, wherein the interrogator further comprises a wire that connects the optical head to the transceiver.

4. The neural communication system of claim 3, wherein the wire comprises a fiber optic cable.

5. The neural communication system of claim 2, wherein the transceiver is configured for implantation between skin and a skull of a patient.

6. The neural communication system of claim 2, wherein the transceiver is not implanted within a patient.

7. The neural communication system of claim 1, wherein the optical head is configured for implantation between a dura and a skull of a patient.

8. The neural communication system of claim 1, wherein the optical head is not implanted within a patient.

9. The neural communication system of claim 1, wherein the sensor comprises a microelectrode that contacts the tissue.

10. The neural communication system of claim 1, wherein the microprobe is magnetic such that a magnetic field is able to move the microprobe within the tissue.

11. The neural communication system of claim 1, wherein the transducer of the microprobe is a field effect transistor (FET) in a source-follower configuration or a common source configuration.

12. The neural communication system of claim 1, wherein the interrogator further comprises a reflectometer that is configured to measure power of the modulated light signal.

13. The neural communication system of claim 12, wherein the reflectometer is configured to produce a map of reflectivity versus depth for the microprobe.

14. The neural communication system of claim 1, wherein the interrogator further comprises a two-dimensional scanner configured to direct the light signal to a plurality of tissue locations to scan an area of interest.

15. The neural communication system of claim 1, wherein the microprobe includes a power harvesting system such that the microprobe receives power by way of the light signal.

16. The neural communication system of claim 15, wherein the power harvesting system includes an electroabsorptive modulator.

17. The neural communication system of claim 16, wherein the power harvesting system also includes a field effect transistor.

18. The neural communication system of claim 1, wherein the light signal comprises a read light signal, and wherein the optical head is also configured to transmit a write light signal to stimulate one or more neurons in the tissue.

19. The neural communication system of claim 1, wherein the light signal follows a transmit path from the optical head to the retroflector, and wherein the reflected modulated light signal follows the transmit path in reverse from the retroflector to the optical head.

20. The neural communication system of claim 1, wherein the interrogator is configured to communicate with at least 1000 microprobes that are in contact with the tissue.

* * * * *